US010376524B2

(12) United States Patent
Parker et al.

(10) Patent No.: US 10,376,524 B2
(45) Date of Patent: *Aug. 13, 2019

(54) USE OF GABA$_A$ RECEPTOR ANTAGONISTS FOR THE TREATMENT OF EXCESSIVE SLEEPINESS AND DISORDERS ASSOCIATED WITH EXCESSIVE SLEEPINESS

(71) Applicant: EMORY UNIVERSITY, Atlanta, GA (US)

(72) Inventors: Kathy P. Parker, Rochester, NY (US); David B. Rye, Dunwoody, GA (US); Andrew Jenkins, Decatur, GA (US)

(73) Assignee: Emory University, Atlanta, GA (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/445,131

(22) Filed: Feb. 28, 2017

(65) Prior Publication Data
US 2017/0196885 A1 Jul. 13, 2017

Related U.S. Application Data

(63) Continuation of application No. 12/922,044, filed as application No. PCT/US2009/037034 on Mar. 12, 2009, now Pat. No. 9,616,070.

(60) Provisional application No. 61/036,047, filed on Mar. 12, 2008.

(51) Int. Cl.
A61K 9/00 (2006.01)
A61K 9/06 (2006.01)
A61K 31/5517 (2006.01)
A61K 31/70 (2006.01)
A61K 9/08 (2006.01)
A61K 9/20 (2006.01)

(52) U.S. Cl.
CPC .......... A61K 31/5517 (2013.01); A61K 9/006 (2013.01); A61K 9/0014 (2013.01); A61K 9/0019 (2013.01); A61K 9/06 (2013.01); A61K 9/08 (2013.01); A61K 9/20 (2013.01); A61K 31/70 (2013.01)

(58) Field of Classification Search
None
See application file for complete search history.

(56) References Cited

U.S. PATENT DOCUMENTS

| 5,811,088 | A | 9/1998 | Hunter et al. |
|---|---|---|---|
| 6,319,926 | B1 | 11/2001 | Cotrel et al. |
| 6,503,950 | B1 | 1/2003 | Ockert |
| 6,977,070 | B2 | 12/2005 | Dugger, III |
| 2002/0058656 | A1 | 5/2002 | Ockert |
| 2002/0166135 | A1 | 11/2002 | Waleh et al. |
| 2005/0031688 | A1 | 2/2005 | Ayala |
| 2008/0317843 | A1 | 12/2008 | Jenkins et al. |
| 2011/0028418 | A1 | 2/2011 | Parker et al. |

FOREIGN PATENT DOCUMENTS

| WO | 200051590 A2 | 9/2000 |
|---|---|---|
| WO | 200158439 A1 | 8/2001 |
| WO | 2003068186 A1 | 8/2003 |
| WO | 2003077897 A1 | 9/2003 |
| WO | 2005063248 | 7/2005 |

OTHER PUBLICATIONS

U.S. Appl. No. 12/922,044, Final Office Action dated Mar. 16, 2016, 16 pages.
U.S. Appl. No. 12/922,044, Final Office Action dated Dec. 19, 2014, 20 pages.
U.S. Appl. No. 12/922,044, Final Office Action dated Dec. 28, 2012, 17 pages.
U.S. Appl. No. 12/922,044, Non-Final Office Action dated Jul. 6, 2012, 15 pages.
U.S. Appl. No. 12/922,044, Non-Final Office Action dated May 22, 2014, 15 pages.
U.S. Appl. No. 12/922,044, Non-Final Office Action dated Sep. 14, 2015, 20 pages.
U.S. Appl. No. 12/922,044, Notice of Allowance dated Nov. 28, 2016, 10 pages.
Arnulf et al., Abnormal sleep and sleepiness in Parkinson's disease, Current Opinion in Neurology, vol. 21(4), 2008, pp. 472-477.
Bassetti et al., Idiopathic hypersomnia. A series of 42 patients, vol. 120, Aug. 1, 1997, pp. 1423-1435.
Cortelli et al., Endozepines in recurrent stupor, Sleep Medicine Reviews, vol. 9 (6), Oct. 17, 2005, pp. 477-487.
Dauvilliers et al., Hypersomnia, Dialogues in Clinical Neuroscience, vol. 7, No. 4, Dec. 2005, pp. 347-356.
Editor'S Summary, Awake and Refreshed, Sci. Transl. Med., vol. 4, 161ra151, 2012.
European Application No. 09719372, Extended European Search Report dated Jun. 1, 2011, 7 pages.
Gottesmann, Commentary: GABA Mechanisms and Sleep, Neuroscience, vol. 3(2), 2002, pp. 231-239.
Granot et al., Endozepine Stupor: Disease or Deception? A Critical Review, Sleep, vol. 27(8), Dec. 15, 2004, pp. 1597-1599.

(Continued)

Primary Examiner — Layla D Berry
Assistant Examiner — Bahar Craigo
(74) Attorney, Agent, or Firm — Kilpatrick Townsend & Stockton LLP

(57) ABSTRACT

GABA$_A$ receptor mediated hypersomnia can be treated by administering a GABA$_A$ receptor antagonist (e.g., flumazenil; clarithromycin; picrotoxin; bicuculline; cicutoxin; and oenanthotoxin). In some embodiments, the GABA$_A$ receptor antagonist is flumazenil or clarithromycin. The GABA$_A$ receptor mediated hypersomnia includes shift work sleep disorder, obstructive sleep apnea/hypopnea syndrome, narcolepsy, excessive sleepiness, hypersomnia (e.g., idiopathic hypersomnia; recurrent hypersomnia; endozepine related recurrent stupor; and amphetamine resistant hypersomnia), and excessive sleepiness associated with shift work sleep disorder, obstructive sleep apnea/hypopnea syndrome, and hypersomnia (e.g., idiopathic hypersomnia; recurrent hypersomnia; endozepine related recurrent stupor; and amphetamine resistant hypersomnia.

19 Claims, 11 Drawing Sheets

(56) References Cited

OTHER PUBLICATIONS

Holzer et al., Transient Apnoea after Systemic Injection of GABA in the Rat, Naunyn-Schmiedeberg's Archives of Pharmacology. vol. 308(1), 1979, pp. 55-60.

Kaczynska et al., Apnoeic response to stimulation of peripheral GABA receptors in rats, Respiratory Physiology & Neurobiology, vol. 131(3), Aug. 1, 2002, pp. 189-197.

Leibowitz et al., Differential Diagnosis and Treatment of Excessive Daytime Sleepiness, Primary Psychiatry, vol. 12, No. 8, Aug. 1, 2005, pp. 57-66.

Lugaresi et al., Endozepine stupor: Recurring stupor linked to endozepine-4 accumulation, Brain, vol. 121, 1998, pp. 127-133.

Lugaresi et al., Suspected covert lorazepam administration misdiagnosed as recurrent endozepine stupor, Brain. vol. 121 (Pt 11), 1998, p. 2201.

Mayo Clinic Staff, Parkinson's disease, Available online at: http://www.mayoclinic.com/health/parkinsonsdisease/DS00295, Jun. 28, 2012, 11 pages.

Minzenberg et al., Modafinil: A Review of Neurochemical Actions and Effects on Cognition, Neuropsychopharmacology, vol. 33, issue 7, 2008, pp. 1477-1502.

Ogden, Mean Body Weight, Height, and Body Mass Index, United States 1960-2002, Advance Data: From Vital and Health Statistics, No. 347, 2004, 18 pages.

Ozone et al., Pharmacology: The effects of flumazenil on sleepiness, task performance and nocturnal sleep after anesthesia and midazolam, Psychiatry and Clinical Neurosciences, vol. 55, 2001, pp. 235-237.

Pietro et al., Endozepines in recurrent stupor, Sleep Medicine Reviews, vol. 9, No. 6, Dec. 2005, pp. 477-487.

Riva et al., Spinning more yarn: endozepine, The Lancet, vol. 351, No. 9109, Apr. 11, 1998, p. 1138.

Rothstein et al., Purification and characterization of naturally occurring benzodiazepine receptor ligands in rat and human brain, vol. 58, No. 6, Jun. 1992, pp. 2102-2115.

Rye et al., Modulation of vigilance in the primary hypersomnias by endogenous enhancement of GABAA receptors, Sci. Transl. Med., vol. 4, 161ra151, 2012, pp. 1-12.

Sanford et al., The influence of age, gender, ethnicity, and insomnia on Epworth sleepiness scores: A normative US population, Sleep Medicine, vol. 7 (4), 2006, pp. 319-326.

Simini et al., Endozepine yarn, The Lancet, vol. 351, No. 9100, Feb. 7, 1998, p. 458.

Vgontzas et al., Sleep and Its Disorders, Annu. Rev. Med vol. 50, 1999, pp. 387-400.

Yamada et al., Respiratory Depression produced by activation of GABA receptors in hindbrain of cat, Journal of Applied Physiology Respiratory Environmental and Exercise Physiology, vol. 51(5), 1981, pp. 1278-1286.

Yamada, Treatment of recurrent hypersomnia with methylcobalamin (vitamin B12): A case report, Psychiatry and clinical Neurosciences, vol. 49, No. 5-6, Dec. 1995, pp. 305-307.

USE OF GABA$_A$ RECEPTOR ANTAGONISTS FOR THE TREATMENT OF EXCESSIVE SLEEPINESS AND DISORDERS ASSOCIATED WITH EXCESSIVE SLEEPINESS

CROSS-REFERENCE TO RELATED APPLICATIONS

This application is a continuation of U.S. patent application Ser. No. 12/922,044, filed Sep. 10, 2010, which is a filing under 35 U.S.C. § 371 based on PCT/US2009/037034 filed Mar. 12, 2009, which claims priority under 35 U.S.C. § 119 to U.S. Provisional Application Ser. No. 61/036,047, filed Mar. 12, 2008, each of which applications are incorporated by reference in their entirety herein.

TECHNICAL FIELD

The present disclosure relates to the treatment of excessive sleepiness and promotion of wakefulness in a subject. In particular, a method of treating hypersomnia (e.g., GABA$_A$ receptor mediated hypersomnia) using a GABA$_A$ receptor anagonist such as flumazenil (formulated, for example, for I.V., transdermal, transmucosal, sublingual, or subdermal administration) is disclosed.

BACKGROUND

There are two main categories of hypersomnia: primary hypersomnia (sometimes called idiopathic hypersomnia) and recurrent hypersomnia (sometimes called idiopathic recurrent hypersomnia). Both are characterized by similar signs and symptoms and differ only in the frequency and regularity with which the symptoms occur.

Primary hypersomnia is characterized by excessive daytime sleepiness over a long period of time. The symptoms are present all, or nearly all, of the time. Recurring hypersomnia involves periods of excessive daytime sleepiness that can last from one to many days, and recur over the course of a year or more. The primary difference between this and primary hypersomnia is that persons experiencing recurring hypersomnia will have prolonged periods where they do not exhibit any signs of hypersomnia, whereas persons experiencing primary hypersomnia are affected by it nearly all the time. Idiopathic hypersomnia is much like narcolepsy, except there is no cataplexy, no sleep paralysis, and no rapid eye movement when the victim first falls asleep.

Various treatments including prescription drugs have been used to treat hypersomnia without significant success, and no substantial body of evidence supports the effectiveness of any of these treatments. Stimulants are not generally recommended to treat hypersomnia as they treat the symptoms but not the base problem. There is a need for more effective treatments of hypersomnia, especially using administration routes that allow for better drug delivery and patient compliance.

SUMMARY

The inventors have discovered that many patients that suffer from excessive sleepiness or disorders associated with excessive sleepiness have one or more endogenous substances present, typically in excess, in their CSF that act as positive allosteric modulators of the GABA$_A$ receptor, potentiating the effect of GABA on the receptor. Treatment of such patients with a GABA$_A$ receptor antagonist thus can provide a method to treat the disorders, in particular the symptoms of excessive sleepiness associated with the disorders.

Accordingly, provided herein are methods of treating GABA$_A$ receptor mediated hypersomnia in a subject, the methods comprising administering to the subject an effective amount of a GABA$_A$ receptor antagonist. In addition, provided herein is a method of treating excessive sleepiness associated with GABA$_A$ receptor mediated hypersomnia in a subject, comprising administering to the subject an effective amount of a GABA$_A$ receptor antagonist. In some embodiments, the GABA$_A$ receptor mediated hypersomnia is selected from one or more of: shift work sleep disorder; narcolepsy; obstructive sleep apnea/hypopnea syndrome; REM behavior disorder; frontal nocturnal dystonia; restless legs syndrome; nocturnal movement disorder; Kleine-Levin syndrome; Parkinson's disease; excessive sleepiness; hypersomnia; idiopathic hypersomnia; recurrent hypersomnia; endozepine related recurrent stupor; and amphetamine resistant hypersomnia. In some embodiments, the GABA$_A$ receptor mediated hypersomnia is a result of the production of endogenous somnogenic compounds in a subject, e.g., excessive amounts of somnogenic compounds. In some embodiments, the GABA$_A$ receptor antagonist can be a negative allosteric modulator. In some embodiments, the GABA$_A$ receptor antagonist is selected from the group consisting of: flumazenil; clarithromycin; picrotoxin; bicuculline; cicutoxin; and oenanthotoxin. In some embodiments, the method includes administering an I.V., transdermal, transmucosal, sublingual, or subdermal formulation of the GABA$_A$ receptor antagonist to the subject.

Also provided herein is a method of treating excessive sleepiness in a subject. The method comprises the steps of determining whether the subject has an endogenously produced somnogenic compound in a CSF sample of the subject, e.g., an excessive amount of the somnogenic compound; and administering to the subject an effective amount of a GABA$_A$ receptor antagonist, e.g., flumazenil. The step of determining whether the subject has an endogenously produced somnogenic compound, including an excessive amount of the somnogenic compound, includes the steps of: a) measuring the potentiation of GABA$_A$ receptors contacted with the CSF sample of the subject in a whole cell patch clamp assay, wherein the cells express benzodiazepine sensitive receptors; b) measuring the potentiation of GABA$_A$ receptors contacted with the CSF sample of the subject in a whole cell patch clamp assay, wherein the cells express benzodiazepine insensitive receptors; and c) comparing the response of step a) to the response of step b), wherein a persistence of potentiation in step b) to within ±25% of the step a) response is indicative of an endogenously produced somnogenic compound in the CSF sample of the subject. In some embodiments, the somnogenic compound is a non-classical benzodiazepine. In some embodiments, the somnogenic compound binds to a site on the GABA$_A$ receptor, e.g., an allosteric site. In some embodiments, the site on the GABA$_A$ receptor is other than the benzodiazepine binding site.

A method of treating excessive sleepiness of a subject endogenously producing a somnogenic compound, e.g., an excessive amount of a somnogenic compound, is also provided herein, the method comprising administering to the subject an effective amount of a GABA$_A$ receptor antagonist, e.g., flumazenil. Further described herein is a method of determining whether a subject will benefit from treatment with a GABA$_A$ receptor antagonist, e.g., flumazenil, wherein the benefit is a reduction in excessive sleepiness, the method comprising determining whether the subject has an endogenously produced somnogenic compound, e.g., an excess of the somnogenic compound, in a CSF sample of the subject, wherein the presence of the endogenously produced somnogenic compound is indicative that the subject will benefit from treatment with $GABA_A$ receptor antagonist, e.g., flumazenil. In the method, the determining step comprises: a) measuring the potentiation of $GABA_A$ receptors contacted with the CSF sample of the subject in a whole cell patch clamp assay, wherein the cells express benzodiazepine sensitive receptors; b) measuring the potentiation of $GABA_A$ receptors contacted with the CSF sample of the subject in a whole cell patch clamp assay, wherein the cells express benzodiazepine insensitive receptors; and c) comparing the response of step a) to the response of step b), wherein a persistence of potentiation to within ±25% of the step a) response is indicative that the subject will benefit from treatment with flumazenil.

In some embodiments of the methods described herein, the $GABA_A$ receptor antagonist is a negative allosteric modulator. In some embodiments, the $GABA_A$ receptor antagonist is selected from the group consisting of: flumazenil; clarithromycin; picrotoxin; bicuculline; cicutoxin; and oenanthotoxin. In some embodiments, the $GABA_A$ receptor antagonist is flumazenil. In some embodiments, the $GABA_A$ receptor antagonist is clarithromycin.

Further provided herein are methods of treating disorders associated with excessive sleepiness (e.g., $GABA_A$ receptor mediated hypersomnia) and symptoms of excessive sleepiness in a subject. In some embodiments, the method includes administering an I.V., transdermal, transmucosal, sublingual, or subdermal formulation of a $GABA_A$ receptor antagonist, e.g., selected from flumazenil; clarithromycin; picrotoxin; bicuculline; cicutoxin; and oenanthotoxin to the subject.

A disorder associated with excessive sleepiness can be selected from one or more of: shift work sleep disorder; narcolepsy; obstructive sleep apnea/hypopnea syndrome; hypersomnia; REM behavior disorder; frontal nocturnal dystonia; restless legs syndrome; nocturnal movement disorder; Kleine-Levin syndrome; and Parkinson's disease. In some embodiments, the disorder is hypersomnia, for example $GABA_A$ receptor mediated hypersomnia (e.g., idiopathic hypersomnia; recurrent hypersomnia; endozepine related recurrent stupor; and amphetamine resistant hypersomnia).

A method of treating a disorder associated with excessive sleepiness in a subject is provided, the method comprising administering to the subject an effective amount of a transmucosal, transdermal, or I.V. formulation of a $GABA_A$ receptor antagonist, e.g., flumazenil. In some embodiments, treating a disorder associated with excessive sleepiness can include administering an effective amount of a $GABA_A$ receptor antagonist, e.g., flumazenil, using a subdermal pump.

In some embodiments, a transmucosal formulation of a $GABA_A$ receptor antagonist, e.g., flumazenil, is administered. The transdermal formulation can be administered supralingually, sublingually, or buccally.

In some embodiments, the subject is administered about 2 mg flumazenil per Body Mass Index unit of the subject over a 24 hour period. Administration may be self-administered by the patient as needed, or in the case of an I.V. or subdermal route of administration, the flumazenil can be administered automatically. In some embodiments, the effective amount of flumazenil is about 6 mg per dose six times per day.

Independent of the formulation and route of administration, any of the methods may further comprise administering a wakefulness promoting agent (e.g., modafinil and armodafinil). In some embodiments, the wakefulness promoting agent is modafinil. In some embodiments, the method comprises administering a time-release formulation of a $GABA_A$ receptor antagonist, such as a time-release transdermal formulation.

Further provided herein is a method of treating a $GABA_A$ receptor mediated hypersomnia in a subject, the method comprising: a) administering to the subject a sublingual formulation of a $GABA_A$ receptor antagonist, e.g., flumazenil; and b) administering to the subject a wakefulness promoting agent. In some embodiments, the method comprises: a) administering flumazenil in an amount of about 2 mg of flumazenil per Body Mass Index unit of the subject per 24 hour period; and b) administering to the subject a wakefulness promoting agent. Also provided is a method of treating a $GABA_A$ receptor mediated hypersomnia in a subject, the method comprising: a) administering to the subject a $GABA_A$ receptor antagonist, e.g., flumazenil, using a subdermal pump; and b) administering to the subject a wakefulness promoting agent. In some embodiments, a method of treating a $GABA_A$ receptor mediated hypersomnia in a subject is provided, the method comprising: a) administering to the subject an I.V. formulation of flumazenil in an amount of about 0.2 mg to about 2 mg; and b) administering to the subject a wakefulness promoting agent. In some embodiments, the methods described above further comprise administration of a transdermal formulation of a $GABA_A$ receptor antagonist, e.g., flumazenil.

A method of treating a disorder associated with excessive sleepiness in a subject is provided, the method comprising administering a $GABA_A$ receptor antagonist, e.g., flumazenil, in an amount effective to decrease the subject's CSF-induced enhancement of whole cell patch clamp assayed $GABA_AR$ responses in the presence of GABA such that the responses in the presence of GABA are within ±25% of a control sample. In some embodiments, a method of treating a disorder associated with excessive sleepiness in a subject is provided, the method comprising administering a $GABA_A$ receptor antagonist, e.g., flumazenil, in an amount effective to modulate the response of a CSF sample of the subject as measured in a GABA whole cell patch clamp assay to within ±25% of the response of a control sample. In some embodiments, the modulation is a decrease in the response of the CSF sample of the subject in the presence of a $GABA_A$ receptor antagonist, e.g., flumazenil.

A method of testing a subject for the presence of a positive allosteric modulator of $GABA_A$ receptor function in a CSF or blood sample is also provided, the method comprising measuring the response of $GABA_A$ Receptors contacted with the CSF or blood and with GABA in a whole cell patch clamp assay, and comparing the response to a control sample, wherein a greater than 50% increase in the response relative to the control is indicative of the presence of a positive allosteric modulator of $GABA_A$ receptor function.

Also provided herein are methods of treating shift work sleep disorder, obstructive sleep apnea/hypopnea syndrome, and narcolepsy in a subject, the methods comprising administering to the subject an effective amount of a $GABA_A$ receptor antagonist, e.g., flumazenil. A method of treating excessive sleepiness associated with shift work sleep disorder, obstructive sleep apnea/hypopnea syndrome, hypersomnia (e.g., idiopathic hypersomnia; recurrent hypersomnia; endozepine related recurrent stupor; and amphetamine resistant hypersomnia), or narcolepsy in a subject is also provided, the method comprising administering to the subject an effective amount of a $GABA_A$ receptor antagonist, e.g., flumazenil. In some embodiments, the a $GABA_A$ receptor antagonist is an I.V. formulation, a transdermal formulation, or a transmucosal formulation.

A method of altering a somnolent state of a subject is further provided herein, the method comprising administering to the subject an effective amount of a $GABA_A$ receptor antagonist, e.g., flumazenil. The somnolent state is selected from one or more of: narcolepsy, obstructive sleep apnea/hypopnea syndrome, shift work sleep disorder, and hypersomnia (e.g., idiopathic hypersomnia; recurrent hypersomnia; endozepine related recurrent stupor; and amphetamine resistant hypersomnia). In some embodiments, the a $GABA_A$ receptor antagonist is an I.V. formulation, a transdermal formulation, or a transmucosal formulation.

Also provided herein are methods for enhancing alertness or increasing regularity of sleep rhythms in a subject; promoting wakefulness in a subject; improving cognitive dysfunction in a subject; and restoring a normal sleep pattern and improving the quality of psychosocial life and relationships in a subject, each method comprising administering to the subject an effective amount of a $GABA_A$ receptor antagonist, e.g., flumazenil. In some embodiments, the a $GABA_A$ receptor antagonist is an I.V. formulation, a transdermal formulation, or a transmucosal formulation.

A method of characterizing the phenotypic spectrum of $GABA_A$ receptor mediated hypersomnia is also provided, the method comprising measuring the potentiation of $GABA_A$ receptor function of a CSF or plasma sample of at least one subject having a disorder associated with excessive sleepiness, and correlating the potentiation with at least one measure of sleep or sleepiness of the subject, wherein a positive correlation is indicative that the subject's disorder is within the phenotypic spectrum of a $GABA_A$ receptor mediated hypersomnia. In some embodiments, the measure of sleep and sleepiness is a behavioral assessment, an electroencephalographic assessment, or a subjective assessment. The method can further comprise quantifying $GABA_A$ receptor function.

Further provided herein are uses of a $GABA_A$ receptor antagonist such as flumazenil for the manufacture of medicaments for the treatment of the following disorders and conditions: obstructive sleep apnea/hypopnea syndrome; shift work sleep disorder; narcolepsy; hypersomnia; and excessive sleepiness associated with shift work sleep disorder, obstructive sleep apnea/hypopnea syndrome, hypersomnia, or narcolepsy. In some embodiments, the hypersomnia is selected from one or more of: idiopathic hypersomnia; recurrent hypersomnia; endozepine related recurrent stupor; and amphetamine resistant hypersomnia.

Also provided herein are uses of a $GABA_A$ receptor antagonist such as flumazenil for the manufacture of medicaments for altering a somnolent state of a subject; enhancing alertness or increasing regularity of sleep rhythms in a subject; promoting wakefulness in a subject; improving cognitive dysfunction in a subject; and restoring a normal sleep pattern and improving the quality of psychosocial life and relationships in a subject. In some embodiments, the somnolent state is selected from one or more of: narcolepsy; obstructive sleep apnea/hypopnea syndrome; shift work sleep disorder; and hypersomnia. In some embodiments, the hypersomnia is selected from one or more of: idiopathic hypersomnia; recurrent hypersomnia; endozepine related recurrent stupor; and amphetamine resistant hypersomnia. In some embodiments, a $GABA_A$ receptor antagonist such as flumazenil is formulated for administration by a transdermal, transmucosal, or intravenous route for the uses described herein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
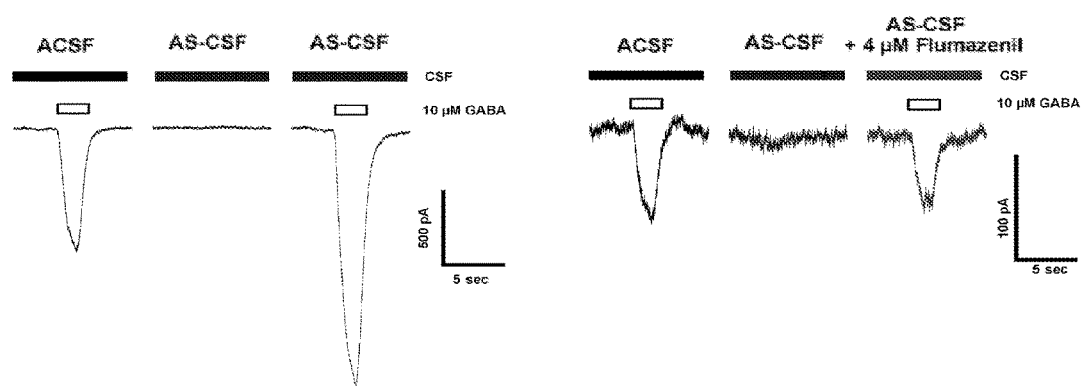
FIG. 1 illustrates whole cell patch clamp recordings of $GABA_AR$ function with and without flumazenil.
Figure 2:
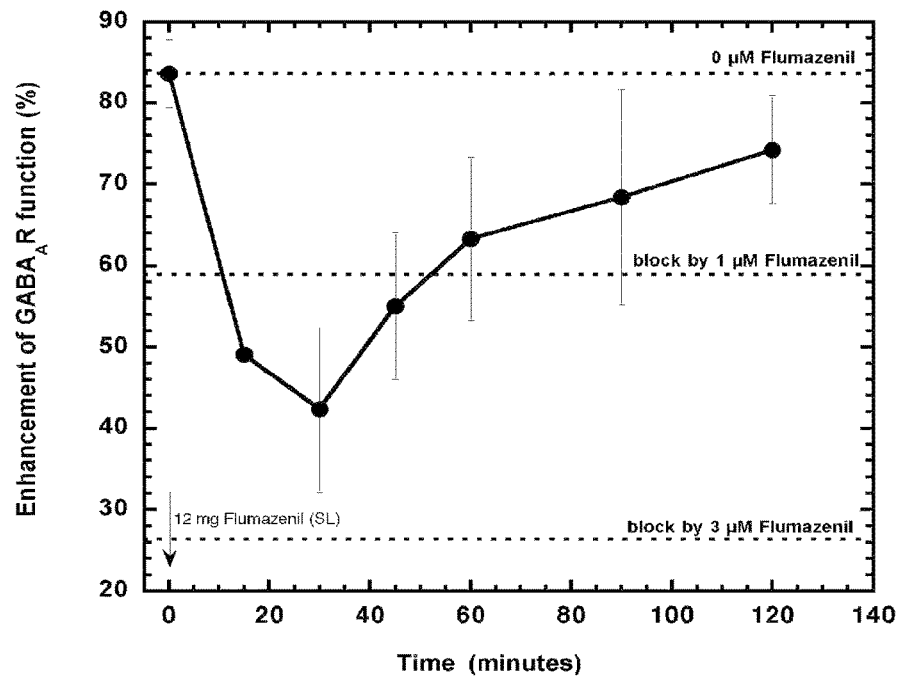
FIG. 2 shows that human α1β2γ2s $GABA_A$ receptor function is enhanced by the plasma of a subject suffering from hypersomnia. Enhancement is reduced following administration of 12 mg of a sublingual formulation of flumazenil.

Ionotropic $GABA_A$ receptors ($GABA_AR$) are the most recognized therapeutic targets for anesthetics and sedative/hypnotic drugs. Mutations in the α1, γ2, and delta subunits of $GABA_A$ R account for several of the heritable epilepsies, endogenous positive allosteric neurosteroid modulators contribute to fluctuations in mood due to developmental changes in expression of the α4δ. $GABA_AR$, and mutation of the β3 subunit has been associated with chronic insomnia. The inventors have found that a naturally occurring endogenous, positive, allosteric modulator of recombinant α1, β2, γ2 short splice variant $GABA_AR$ is present in CSF plasma in normal humans and non-human primates, and when present in excess, produces hypersomnia and excessive daytime sleepiness, or $GABA_A$ receptor mediated hypersomnia (GRH) as described herein. Accordingly, treatment of such patients with a $GABA_A$ receptor antagonist thus can provide a method to treat patients having various disorders associated with excessive sleepiness, and in particular treat the symptoms of excessive sleepiness associated with the various disorders.

I. Methods of Treating $GABA_A$ Receptor Mediated Hypersomnia and Disorders Associated with Excessive Sleepiness Provided herein are methods of treating $GABA_A$ receptor mediated hypersomnia in a subject, the methods comprising administering to the subject an effective amount of a $GABA_A$ receptor antagonist. In addition, provided herein is a method of treating excessive sleepiness associated with $GABA_A$ receptor mediated hypersomnia in a subject, comprising administering to the subject an effective amount of a $GABA_A$ receptor antagonist. In some embodiments of the methods described herein, the $GABA_A$ receptor antagonist is a negative allosteric modulator. In some embodiments, the $GABA_A$ receptor antagonist is selected from the group consisting of: flumazenil; clarithromycin; picrotoxin; bicuculline; cicutoxin; and oenanthotoxin. In some embodiments, the $GABA_A$ receptor antagonist is flumazenil. In some embodiments, the $GABA_A$ receptor antagonist is clarithromycin. In some embodiments, the method includes administering a I.V., transdermal, transmucosal, sublingual, or subdermal formulation of flumazenil to the subject. The administration of flumazenil can be combined with administration of other agents, including wakefulness promoting agents and transdermal formulations of flumazenil.

$GABA_A$ receptor mediated hypersomnia or disorders associated with excessive sleepiness are selected from one or more of: shift work sleep disorder; narcolepsy; obstructive sleep apnea/hypopnea syndrome; REM behavior disorder; frontal nocturnal dystonia; restless legs syndrome; nocturnal movement disorder; Kleine-Levin syndrome; Parkinson's disease; excessive sleepiness; hypersomnia; idiopathic hypersomnia; recurrent hypersomnia; endozepine related recurrent stupor; and amphetamine resistant hypersomnia. In some embodiments, the $GABA_A$ receptor mediated hypersomnia is selected from idiopathic hypersomnia; recurrent hypersomnia; endozepine related recurrent stupor; and amphetamine resistant hypersomnia. In some embodiments, the hypersomnia is idiopathic hypersomnia. In some embodiments, the hypersomnia is endozepine related recurrent stupor. In some embodiments, the hypersomnia is amphetamine resistant hypersomnia.

Such disorders can be characterized by many objective and subjective tests known in the art. For example, the Epworth Sleepiness Scale; the Stanford Sleepiness Scale; the Pittsburgh Sleep Quality Index; an Activity-Rest and Symptom Diary; Actigraphy; Psychomotor Vigilance Task; Polysomnography; Functional Magnetic Resonance Imaging; Profile of Mood States; Functional Outcomes of Sleep Questionnaire; Medical Outcomes Study Short-Form 36; and Neurophysical Testing, such as the Cambridge Neurophysical Test Automated Battery (CANTAB) (e.g., physcomotor speed, attention, working memory, and executive function).

In addition, $GABA_A$ receptor mediated hypersomnia can be characterized by demonstration of enhanced $GABA_A$ Receptor function of a subject's CSF or plasma as compared to a control, e.g., see Example 1 and Example 14.

II. Methods of Promoting Wakefulness and Enhancing Alertness in Sleepiness Associated Disorders Further provided herein are methods of treating $GABA_A$ mediated hypersomnia disorders, including shift work sleep disorder, obstructive sleep apnea/hypopnea syndrome, narcolepsy, and excessive sleepiness associated with shift work sleep disorder, obstructive sleep apnea/hypopnea syndrome, hypersomnia, and narcolepsy. In some embodiments, the $GABA_A$ mediated hypersomnia is idiopathic hypersomnia; recurrent hypersomnia; endozepine related recurrent stupor; or amphetamine resistant hypersomnia. The method comprises administering to the subject an effective amount of a $GABA_A$ receptor antagonist, such as flumazenil. In some embodiments, the $GABA_A$ receptor antagonist is an I.V. formulation, a transdermal formulation, or a transmucosal formulation.

A method of altering a somnolent state of a subject is further provided herein, the method comprising administering to the subject an effective amount of $GABA_A$ receptor antagonist, e.g., flumazenil. The somnolent state is selected from one or more of: narcolepsy, obstructive sleep apnea/hypopnea syndrome, shift work sleep disorder, and hypersomnia (e.g., idiopathic hypersomnia; recurrent hypersomnia; endozepine related recurrent stupor; and amphetamine resistant hypersomnia). In some embodiments, the $GABA_A$ receptor antagonist is an I.V. formulation, a transdermal formulation, or a transmucosal formulation.

Also provided herein are methods for enhancing alertness or increasing regularity of sleep rhythms in a subject; promoting wakefulness in a subject; improving cognitive dysfunction in a subject; and restoring a normal sleep pattern and improving the quality of psychosocial life and relationships in a subject, each method comprising administering to the subject an effective amount of $GABA_A$ receptor antagonist, e.g., flumazenil. In some embodiments, the $GABA_A$ receptor antagonist is an I.V. formulation, a transdermal formulation, or a transmucosal formulation.

As used herein, the term "promoting wakefulness" refers to a decrease in sleepiness, tendency to fall asleep, or other symptoms of undesired or reduced alertness or consciousness compared with sleepiness, tendency to fall asleep, or other symptoms of undesired or reduced alertness or consciousness expected or observed without treatment. Promoting wakefulness refers to a decrease in any stage of sleep, including light sleep, deeper sleep characterized by the presence of high amplitude, low wave brain activity termed "slow wave sleep", and rapid eye movement (REM) sleep.

A determination of whether the treatment is useful in performing the methods described herein can be made, for example, by direct observation of behavioral or physiological properties of mammalian sleep, by self-reporting, or by various well-known methods, including electrophysiological methods. Such methods include, for example, examining electroencephalograph (EEG) activity amplitude and frequency patterns, examining electromyogram activity, and examining the amount of time during a measurement time period, in which a mammal is awake or exhibits a behavioral or physiological property characteristic of wakefulness.

The effectiveness of the treatments can also be characterized by the objective and subjective tests described herein, including the Epworth Sleepiness Scale; the Stanford Sleepiness Scale; the Pittsburgh Sleep Quality Index; an Activity-Rest and Symptom Diary; Actigraphy; Psychomotor Vigilance Task; Polysomnography; Functional Magnetic Resonance Imaging; Profile of Mood States; Functional Outcomes of Sleep Questionnaire; Medical Outcomes Study Short-Form 36; and Neurophysical Testing, such as the Cambridge Neurophysical Test Automated Battery (CANTAB) (e.g., physcomotor speed, attention, working memory, and executive function).

III. Formulation and Administration of a $GABA_A$ Receptor Antagonist

A $GABA_A$ receptor antagonist can be selected from flumazenil; clarithromycin; picrotoxin; bicuculline; cicutoxin; and oenanthotoxin and can be formulated for I.V., transdermal, transmucosal, sublingual, oral, and subdermal administration for use with the methods described herein. A transmucosal formulation can include sublingual, supralingual, and buccal administration. For transmucosal administration, the antagonist may be combined with one or more inactive ingredients for the preparation of a tablet, packed powder, edible film strip, soft gel capsule, hard gel capsule, lozenge, or troches. For example, in some embodiments, the antagonists such as flumazenil may be combined with at least one excipient such as fillers, binders, humectants, disintegrating agents, solution retarders, absorption accelerators, wetting agents absorbents, or lubricating agents. According to some embodiments, the antagonist may be combined with one or more of a polyol (e.g., lactose, sucrose, mannitol, or mixtures thereof), an alcohol (e.g., ethanol), and a gum (e.g., acacia and guar), and then formed into a lozenge by conventional methods.

In some embodiments, the formulation is a hard, compressed, rapidly dissolving tablet adapted for direct sublingual dosing. The tablet includes particles made of the antagonist and a protective material. In some embodiments, these particles are provided in an amount of between about 0.01 and about 75% by weight based on the weight of the tablet (e.g., 1%, 5%, 10%, 15%, 20%, 25%, 30%, 35%, 45%, 50%, 60%, 70%, and 75%). In some embodiments, the tablet may also include a matrix made from a nondirect compression filler, a wicking agent, and a hydrophobic lubricant. In some embodiments, the tablet is adapted to dissolve spontaneously in the mouth of a patient in less than about 60 seconds (and, in some cases, in less than about 30 seconds).

In some embodiments, the formulation can be a compressed rapidly dissolving tablet comprising effervescent agents. These effervescent agents allow enhanced adsorption of the antagonist across the mucosal membranes (e.g., tongue, cheek, and gums) in the oral cavity. An example of effervescent pharmaceutical compositions suitable for use in conjunction with the methods described herein are the compositions described in U.S. Pat. No. 6,200,604.

In some embodiments, the antagonist can be administered transmucosally using an edible film. Such films can include a carrier comprising water-soluble polymers in combination with certain ingredients and provides a therapeutic effect. In some embodiments, the film is coated and dried utilizing existing coating technology and exhibits instant wettability followed by rapid dissolution/disintegration upon administration in the oral cavity. In some embodiments, an edible film can contain as the essential components a water-soluble polymer or a combination of water-soluble polymers, one or more plasticizers or surfactants, one or more polyalcohols, and flumazenil. Non-limiting examples of edible films can be found in U.S. Pat. Nos. 5,948,430; 6,177,096; 6,284,264; 6,592,887; and 6,709671.

Further examples of additional pharmaceutical compositions suitable for transmucosal administration include those described in U.S. Pat. Nos. 5,178,878; 5,223,264; and 6,024,981.

In some embodiments, the antagonist is combined with inactive ingredients. Such ingredients may be necessary, for example, to add bulk to the pharmaceutical preparation, to bind the preparation, to add color or flavor to the preparation, and to prevent degradation or growth of contaminants.

In some embodiments, administration of the antagonist may be performed using an implantable device, for example, an implantable, self-regulating mechanochemical subdermal pump. In some embodiments, the device may administer the antagonist on a set dosage program. In some embodiments, the device may administer the antagonist on demand as determined by the subject. In some embodiments, the device may administer the antagonist on a constant release profile. In some embodiments, the device may administer the antagonist automatically. These devices are known in the art for the treatment of other disorders, for example, diabetes. Non-limiting examples of various embodiments of this mode of administration are detailed in U.S. Pat. Nos. 5,062,841; 5,324,518; and 6,852,104.

In some embodiments, a transmucosal administration of an antagonist may be combined with transdermal administration of the same or another antagonist. Without being bound by theory, such a delivery mechanism may be useful for nocturnal application to assist the subject with morning wakefulness.

Transdermal administration of the antagonist can be accomplished by mixing the antagonist with suitable pharmaceutical carriers, preservatives, optional penetration enhancers, and optional gelling agents to form ointments, emulsions, lotions, solutions, creams, gels, patches or the like, wherein a fixed amount of the preparation is applied onto a certain area of skin.

By the term "suitable pharmaceutical carrier" is meant a non-toxic pharmaceutically acceptable vehicle including, for example, polyethylene glycol, propylene glycol, isopropanol, ethanol, oleic acid, N-methylpyrrolidone, sesame oil, olive oil, wood alcohol ointments, vaseline, and paraffin or a mixture thereof.

Suitable penetration enhancers include, for example, saturated and unsaturated fatty acids and their esters, alcohols, monoglycerides, diethanolamines, N,N-dimethylamines such as linolenic acid, linolenyl alcohol, oleic acid, oleyl alcohol, stearic acid, stearyl alcohol, palmitic acid, palmityl alcohol, myristic acid, myristyl alcohol, 1-dodecanol, 2-dodecanol, lauric acid, decanol, capric acid, octanol, caprylic acid, 1-dodecylazacycloheptan-2-one sold under the trademark AZONE (Nelson Research and Development; Irvine, Calif.), ethyl caprylate, isopropyl myristate, hexamethylene lauramide, hexamethylene palmitate, capryl alcohol, decyl methyl sulfoxide, dimethyl sulfoxide, salicylic acid and its derivatives, N,N-diethyl-m-toluamide, crotamiton, 1-substituted azacycloalkan-2-ones, polyethylene glycol monolaurate and any other compounds compatible with medetomidine and its optically active enantiomers and the packages and having transdermal permeation enhancing activity.

Suitable gelling agents include, for example, hydroxy methyl cellulose, hydroxypropyl cellulose sold under the trademark KLUCEL HF (Hercules Inc.; Wilmington, Del.), tragacanth, sodium alginate, gelatin, methylcellulose, sodium carboxymethylcellulose, and polyvinyl alcohols. Suitable preservatives include, for example, parabens, benzoic acid, and chlorocresol.

Antioxidants can be included in the formulations described herein. Suitable antioxidants include, for example, ascorbyl palmirate, butylated hydroxyanisole, butylated hydroxytoluene, potassium sorbate, sodium bisulfate, sorbic acid, propyl gallate, and sodium metabisulfite.

In some embodiments, the antagonist is administered by a transdermal patch. Adhesives for making transdermal patches for use in the methods described herein include polyisobutylene, silicone based adhesives, and acrylic polymers. The adhesive polymers can be mixed with other excipients such as waxes and oils (e.g., mineral oil). A protective liner can be placed in contact with the adhesive layer to protect against drug release from the patch prior to application. Liners for use with the transdermal patches described herein include, for example, polyethylene terephthalate film, polyester membrane, and polycarbonate film.

The backing membrane of the transdermal patch for use with the methods described herein constitutes the top face surface of the transdermal patch. It may be made of a single layer or film of polymer, or be a laminate of one or more polymer layers and metal foil. Examples of polymers suitable for use in making backing films include, for example, polyester films, ethyl vinyl acetate, polypropylene, polyethylene, and polyvinyl-chloride.

In some embodiments, the administration rate of the drug is 0.1-1000 µg/h through a skin area of about 2-90 cm$^2$ (e.g., 10-30 cm$^2$). The amount of drug delivered into the skin can be controlled by a number of factors including skin patch size, degree of drug loading, the use of rate controlling membranes, permeation enhancers, and the like.

In some embodiments, the transmucosal and/or the transdermal formulation may be a time-release or slow-release formulation. In some embodiments, the transdermal formulation may be a time-release or slow-release formulation. The transmucosal or transdermal formulation described herein may also be formulated so as to provide slow or controlled release of the antagonist using, for example, hydropropylmethyl cellulose in varying proportions to provide the desired release profile, other polymer matrices, gels, permeable membranes, osmotic systems, multilayer coatings, microparticles, liposomes and/or microspheres. In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example, pH, temperature, enzymes, water, or other physiological conditions or compounds. Various mechanisms of drug release exist. For example, in one embodiment, the controlled-release component may swell and form porous openings large enough to release the antagonist after administration to a patient. The term "controlled-release component" means a compound or compounds, such as polymers, polymer matrices, gels, permeable membranes, liposomes and/or microspheres that facilitate the controlled-release of the active ingredient in the pharmaceutical composition. In another embodiment, the controlled-release component is biodegradable, induced by exposure to the aqueous environment, pH, temperature, or enzymes in the body.

The specific dose of an antagonist required to obtain therapeutic benefit in the methods of treatment described herein will, usually be determined by the particular circumstances of the individual patient including the size, weight, age, and sex of the subject, the nature and stage of the disorder being treated, the aggressiveness of the disorder, and the route of administration of the compound.

For transmucosal administration (e.g., sublingual administration), for example, a daily dosage of flumazenil, for example, can range from about 0.5 mg to about 10 mg per Body Mass Index (BMI) unit (e.g., about 0.5 mg to about 5 mg; about 1 mg to about 3 mg; about 1.5 mg to about 4 mg; about 2 mg to about 6 mg; about 1.25 mg to about 8 mg; and about 4 mg to about 10 mg). In some embodiments, a daily dosage of flumazenil can range from about 1 mg per BMI to about 5 mg per BMI. In some embodiments, a daily dosage of flumazenil can be about 1.5 mg per BMI. In some embodiments, a daily dosage of flumazenil can be about 2 mg per BMI unit. In some embodiments, a daily dosage of flumazenil can be about 3 mg per BMI unit. For example, a subject with a BMI of 20 could be administered a daily dosage of about 40 mg of flumazenil, in other words, a daily dosage of 2 mg per BMI unit. Higher or lower doses are also contemplated, as it may be necessary to use dosages outside these ranges in some cases.

The transmucosal formulation can be administered in one single dosage or the daily dosage may be divided, such as being divided equally into two to six times per day daily dosing. In some embodiments, the transmucosal formulation is administered at least twice daily. In some embodiments, the transmucosal formulation is administered at least three times daily. In some embodiments, the transmucosal formulation is administered about every one to six hours (e.g., about every one hour; about every two hours; about every three hours; about every three and a half hours; about every four hours; about every five hours; and about every six hours). In some embodiments, the transmucosal formulation is administered by the subject as needed, e.g., patient controlled titration to a desired end effect (e.g., wakefulness or reduced sleepiness).

A transmucosal formulation may be formulated in a unit dosage form, each dosage containing from about 0.5 to about 20 mg of the antagonist, e.g., flumazenil, per unit dosage (e.g., about 0.5 mg to about 15 mg; about 1 mg to about 10 mg; about 1.5 mg to about 8 mg; about 2 mg to about 7 mg; about 3 mg to about 6 mg; about 4 mg to about 8 mg; about 5 mg to about 10 mg; about 6 mg to about 12 mg; and about 8 mg to about 20 mg). In some embodiments, each dosage can contain about 5 to about 10 mg of the antagonist per unit dosage. In some embodiments, each dosage contains about 6 mg of the antagonist. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

For transdermal administration, for example, a daily dosage of flumazenil can range from about 0.5 mg to about 10 mg (e.g., about 0.5 mg to about 5 mg; about 1 mg to about 3 mg; about 1.5 mg to about 4 mg; about 2 mg to about 6 mg; about 1.25 mg to about 8 mg; and about 4 mg to about 10 mg). In some embodiments, a daily dosage of transdermal flumazenil can range from about 1 mg to about 5 mg. In some embodiments, a daily dosage of transdermal flumazenil can be about 1.5 mg. In some embodiments, a daily dosage of transdermal flumazenil can be about 2 mg. In some embodiments, a daily dosage of transdermal flumazenil can be about 3 mg. Higher or lower doses are also contemplated as it may be necessary to use dosages outside these ranges in some cases.

The transdermal formulation can be administered in one single dosage or the daily dosage may be divided, such as being divided equally into two to six times per day daily dosing. In some embodiments the transdermal formulation is formulated to a concentration of about 0.5 mg to about 10 mg per mL (e.g., about 0.5 mg to about 8 mg per mL; about 1 mg to about 6 mg per mL; about 1.5 mg to about 5 mg per mL; about 3 mg to about 7 mg per mL; about 4 mg to about 10 mg per mL; and about 4 mg to about 8 mg per mL). In some embodiments, the transdermal formulation is formulated to a concentration of about 4 mg per mL. In some embodiments, the transdermal formulation is administered once daily (e.g., before bed). In some embodiments, the transdermal formulation is administered at least twice daily. In some embodiments, the transdermal formulation is administered about every eight to about twenty-four hours (e.g., about every eight hours; about every ten hours; about every twelve hours; about every sixteen hours; about every twenty hours; about every twenty-two hours; and about every twenty-four hours).

A transdermal formulation may be formulated in a unit dosage form, each dosage containing from about 0.5 to about 10 mg of flumazenil per unit dosage (e.g., about 0.5 mg to about 8 mg; about 1 mg to about 5 mg; about 1.5 mg to about 4 mg; about 2 mg to about 6 mg; about 3 mg to about 7 mg; about 4 mg to about 8 mg; and about 5 mg to about 10 mg). In some embodiments, each dosage can contain about 1 to about 4 mg of flumazenil per unit dosage. In some embodiments, each dosage contains about 2 mg of flumazenil. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The components used to formulate the pharmaceutical compositions described above are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The antagonist can be administered in combination with other agents. In one embodiment, the antagonist is administered with a wakefulness promoting agent (e.g., modafinil and armodafinil). In some embodiments, the wakefulness promoting agent is modafinil. In some embodiments, the subject may be resistant to one or more wakefulness promoting agents prior to administration of the antagonist. The wakefulness promoting agent can be administered in an amount less than about 600 mg per day (e.g., less than about 100 mg per day; less than about 200 mg per day; less than about 300 mg per day; less than about 400 mg per day; less than about 500 mg per day; and less than about 600 mg per day). The specific dose of a wakefulness promoting agent required to obtain therapeutic benefit in the methods of treatment described herein will usually be determined by the particular circumstances of the individual subject including the size, weight, age, and sex of the subject, the nature and stage of the disorder being treated, the aggressiveness of the disorder, and the route of administration of the compound. In some embodiments, the wakefulness promoting agent can be administered twice daily. In some embodiments, the wakefulness promoting agent can be administered in an amount of 5 mg per BMI unit. In some embodiments, the wakefulness promoting agent can be administered in an amount of 100 mg per dose. In some embodiments, the subject exhibits resistance to a wakefulness promoting agent prior to administration of the antagonist. In some embodiments, administration of the antagonist can reverse or decrease a subjects resistance to a wakefulness promoting agent.

In some embodiments, treatment of a disorder associated with excessive sleepiness can include the following:
a) transmucosal, e.g., sublingual, administration of an antagonist, e.g., flumazenil; and
b) administration of a wakefulness promoting agent.
In some embodiments, the treatment can further include:
c) transdermal administration of an antagonist, e.g., flumazenil.

For example, in some embodiments, a sublingual formulation of flumazenil is administered about every 2 to 4 hours during the waking hours of the day (e.g., every about 3 to 3.5 hours). In some embodiments, a wakefulness promoting agent is administered from one to three times during the waking hours of the day (e.g., about every 4 hours). In some embodiments, the wakefulness promoting agent is modafinil. In some embodiments, a transdermal or time-release formulation of flumazenil is administered once daily (e.g., before bed).

IV. Assay for $GABA_A$ Receptor Mediated Hypersomnia

The $GABA_A$ receptors are one of several classes of chemically gated ion channels that incorporate the features of both "receptors" and "ion channels" into one membrane protein. These chemically gated channels (ligand gated ion channel: LGIC) can detect extracellular chemical signals such as neurotransmitters released from neighboring cells and in response will open an ion channel to allow specific ions to enter or leave the cell. When this results in a net movement of positive charge into the cell, the cell becomes more electrically positive and thus more excitable. Conversely, when this results in a net flow of negative ions into the cell, the neuron becomes more electrically negative and thus more inhibited. In this way, LGICs act as chemical-to-voltage converters and are fundamental to cell-to-cell communication and neuronal activity. Drugs and chemicals that enhance or block these functions have profound effect on brain circuits and ultimately human behavior. For example, most general anesthetics render patients unconscious by enhancing the function of inhibitory LGICs, the most common of which is the $GABA_A$ receptor.

The most common inhibitory neurotransmitter in the human nervous system is γ-aminobutyric acid or GABA. It is released by neurons at synapses, the specialized junctions between 2 neurons that permits rapid cell-to-cell communication. After leaving the presynaptic neuron and crossing the synaptic gap, the molecules of GABA arrive at the postsynaptic membrane where they can interact with a LGIC, the Type-A GABA receptor ($GABA_AR$). After GABA binds to the receptor, the LGIC changes shape and allows the flow of negatively charged chloride ions into the neuron, which results in the neuron becoming inhibited and unable to pass a message onto another neuron, until GABA unbinds and the inhibition passes.

If $GABA_AR$ function is blocked, then the brain circuits in which they are imbedded experience less inhibition. This can cause the circuits to become hyper-excitable, exhibiting much more excitation than normal. This will result in convulsions and seizures if the block is not removed. This can occur in the presence of a $GABA_AR$ channel blocker toxin or a GABA antagonist. This can also occur in some patients who have inherited forms of epilepsy. In these patients, a $GABA_AR$ gene has mutated to make a dysfunctional $GABA_AR$ that does not function as well as it should.

$GABA_ARS$ are enhanced by many chemicals and drugs. General anesthetics, as already noted, enhance inhibition by making the channels stay open for longer periods of time, increasing the duration of inhibition. This is also true for many neurosteroids (e.g., progesterone metabolites) and for ethanol. $GABA_ARS$ are also a critical binding site for benzodiazepines, such as valium. These important anxiolytic and sedative drugs cause the receptors to bind GABA more tightly, also enhancing inhibition by the receptor.

It is important to note that all of these compounds do not activate the channel. They are all "allosteric modulators". They bind to sites separate from the GABA binding sites and simply enhance or amplify the effect of GABA. In the absence of GABA, physiologic and/or therapeutic concentrations of these different compounds have no effect on the channel. GABA must be present for them to have an effect. Similarly, the benzodiazepine antagonist flumazenil is not a $GABA_AR$ blocker. It occupies the benzodiazepine binding site, thus blocking drugs like valium from acting on the channel. Although it is bound to the receptor, flumazenil does not have an effect on the channel. Its functional effect can only be observed when both GABA and a benzodiazepine are present.

Developed in the late 1970s, the single cell electrophysiology method known as patch clamp is a standard for measuring the function of ion channels in research laboratories. The techniques takes advantage of the high electrical resistance between a cell surface and specially constructed microelectrodes, and capacitative feedback electronics which combine to give ultra low noise (<100 fA) recordings of ions flowing through single ion channels.

Provided herein is a method of diagnosing and treating a patient suffering from hypersomnia associated with the endogenous production of $GABA_A$ receptor modulators, e.g., excessive production of such modulators. There are many reports of hypersomnia disorders in subjects who do not respond well to conventional stimulant (e.g., amphetamine) therapies. These subjects may be suffering from a form of hypersomnia referred to as amphetamine resistant hypersomnia, from an increased production of endozepines (e.g., hemin and protoporphyrin IX), or from an increased production of another substance that binds to the $GABA_A$ receptor. Without being bound by theory, the subject may be producing endogenous benzodiazepines (i.e. "endozepines") or other somnogenic compound(s) that interact directly or indirectly with the benzodiazepine binding site on the $GABA_AR$, enhancing receptor function as classic benzodiazepines such as valium.

Figure 19A:
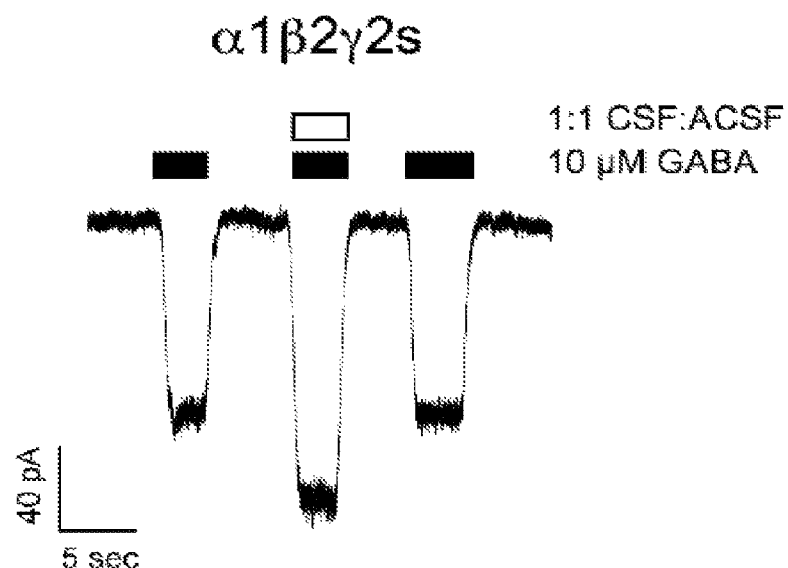
FIG. 19a illustrates a whole cell patch clamp recording from a cell expressing human α1β2γ2s receptors. Bars above the traces indicate duration of GABA and CSF application.
Figure 19B:
FIG. 19b illustrates a whole cell patch clamp recording from a cell expressing the benzodiazepine insensitive subunit α1(H102R). Bars above the traces indicate duration of GABA and CSF application.

A method of diagnosing a patient suffering from $GABA_A$ mediated hypersomnia associated with increased production of endozepines or other somnogenic substance(s) can be performed by measuring the effect of a subjects' cerebral spinal fluid (CSF) or blood or plasma on recombinant $GABA_AR$ function under whole cell patch clamp conditions (see, e.g., FIG. 1 and Example 1 or FIGS. 19A and 19B and Example 14). In some embodiments, the effect of the CSF or blood or plasma can be compared to the effect observed when the CSF or blood or plasma is co-applied with a $GABA_A$ receptor antagonist such as flumazenil. In some embodiments, application of the antagonist such as flumazenil can modulate the response of a CSF or blood sample of a subject as measured in a GABA whole cell patch clamp efficacy assay to within 25% of a control sample response. In some embodiments, the modulation is a decrease in the response of the CSF sample of the subject in the presence of the antagonist such as flumazenil. In some embodiments, the effect of the CSF or blood or plasma in an assay expressing benzodiazepine sensitive receptors can be compared to the effect observed of the CSF or blood or plasma in an assay expressing benzodiazepine insensitive receptors. In some embodiments, the substance in the CSF or blood or plasma sample of a subject potentiates the response of GABA as measured in a GABA whole cell patch clamp efficacy assay. In some embodiments, the potentiation of the GABA response in the benzodiazepine sensitive receptors and the potentiation of the GABA response in the benzodiazepine insensitive receptors are within ±25% of each other. In some embodiments, the persistence of potentiation within ±25% of the GABA responses in benzodiazepine sensitive and insensitive receptor assays is indicative that the subject would benefit from treatment with a $GABA_A$ receptor antagonist. In some embodiments, the $GABA_A$ receptor antagonist is flumazenil.

Further, a method of diagnosing a patient suffering from $GABA_A$ mediated hypersomnia associated with increased production of endozepines or other somnogenic substances can be performed by measuring the effect of a subjects' cerebral spinal fluid (CSF) or blood or plasma on recombinant $GABA_AR$ function under whole cell patch clamp conditions.

V. Kits

Also provided herein are kits for treating disorders associated with excessive sleepiness. A kit can include an I.V., transdermal, oral, or transmucosal (e.g., sublingual, supralingual, and buccal) formulation of a $GABA_A$ receptor antagonist. In some embodiments, the $GABA_A$ receptor antagonist is flumazenil. In some embodiments, the kit can further includes one or more of a wakefulness promoting agent (e.g., modafinil) and a transdermal formulation of a $GABA_A$ receptor antagonist. In some embodiments, a kit can include one or more delivery systems and directions for use of the kit (e.g., instructions for treating a subject). In some embodiments, a kit can include a sublingual formulation of flumazenil and a transdermal formulation of flumazenil. In another embodiment, a kit can include a sublingual formulation of flumazenil and a wakefulness promoting agent. In some embodiments, the kit can include a sublingual formulation of flumazenil and a label that indicates that the contents are to be administered to a subject resistant to amphetamines. In another embodiment, the kit can include a sublingual formulation of a $GABA_A$ receptor antagonist such as flumazenil and a label that indicates that the contents are to be administered to a subject positive for increased production of endozepines or other somnogenic compounds, as described herein. In a further embodiment, a kit can include a sublingual formulation of flumazenil and a label that indicates that the contents are to be administered with a wakefulness promoting agent and/or a transdermal formulation of flumazenil.

Also provided herein are kits for performing a diagnostic assay. In some embodiments, the diagnostic assay can be used to diagnose subjects suffering from a $GABA_A$ receptor mediated hypersomnia and/or to determine subjects that would benefit from treatment with a $GABA_A$ receptor antagonist. In some embodiments, a kit for use as a diagnostic assay is provided with the components for carrying out a patch clamp assay as described herein. In some embodiments, the kit can include a $GABA_A$ receptor antagonist and cells which transiently or stably express human $\alpha 1\beta 2\gamma 2s$ $GABA_A$ receptors. In some embodiments, the kit can include cells which transiently and stably express human $\alpha 1\beta 2\gamma 2s$ $GABA_A$ receptors and cells which transiently and stably express a benzodiazepine insensitive subunit (e.g., $\alpha 1(H102R)$. In some embodiments, the kit further comprises one or more of an extracellular solution that can function as a control sample, e.g., a control CSF sample; an intracellular solution; an extracellular medium, a motor-driven solution exchange device; and instructions for use of the kit.

VI. Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, the singular forms "a," "an," and "the" include plural referents unless the context clearly dictates otherwise.

A "subject" can include both mammals and non-mammals. Mammals include, for example, humans; nonhuman primates, e.g. apes and monkeys; cattle; horses; sheep; rats; mice; pigs; and goats. Non mammals include, for example, fish and birds.

The expression "effective amount", when used to describe an amount of compound in a method, refers to the amount of a compound that achieves the desired pharmacological effect or other effect, for example an amount that results in reduced sleepiness.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

EXAMPLES

Example 1

Endozepine Modulation of $GABA_AR$ Function

HEK293 cells transiently expressing human $\alpha 1$, $\beta 2$, and $\gamma 2s$ subunits were superfused at 1 mL/min with an extracellular solution (ACSF) containing 145 mm NaCl, 3 mm KCl, 1.5 mm $CaCl_2$, 1 mm $MgCl_2$, 6 mm d-glucose, and 10 mm HEPES-NaOH adjusted to pH 7.4. Whole cell patch clamp recordings from cells voltage clamped at –60 mV were made using the Multiclamp 700B amplifier (Molecular Devices, Sunnyvale, Calif.). The resistance of the patch pipette was 4-6 M when filled with intracellular solution (145 mm N-methyl-d-glucamine hydrochloride, 5 mm dipotassium ATP, 1.1 mm EGTA, 2 mm $MgCl_2$, 5 mm HEPES-KOH, and 0.1 mm $CaCl_2$ adjusted to pH 7.2). In addition to the continuous bath perfusion with extracellular medium, solutions including AS99-CSF (as described below), GABA and/or flumazenil were applied rapidly to the cell by local perfusion using a motor-driven solution exchange device (Rapid Solution Changer RSC-160; Molecular Kinetics, Indianapolis, Ind.). Solutions were exchanged within approximately 50 ms. Laminar flow out of the rapid solution changer head was achieved by driving all solutions at identical flow rates (1.0 mL/min) via a multichannel infusion pump (KD Scientific, Holliston, Mass.). The solution changer was driven by protocols in the acquisition program of pCLAMP version 9.2 (Molecular Devices, Sunnyvale, Calif.). AS-CSF was isolated from AS99, a patient experiencing hypersomnia. The patient also exhibited apparent resistance to amphetamine treatment. All other compounds were obtained from the Sigma-Aldrich Co.

Results indicated that AS-CSF had no intrinsic GABA efficacy, but it enhanced the amplitude of response to $EC_{20}$ concentrations of GABA (see FIG. 1a). In a second experiment, 4 µM flumazenil was co-applied with AS-CSF. The flumazenil immediately reversed the enhancing effect of the AS-CSF (see FIG. 1b).

Positive modulation of $GABA_A$ receptor function by 100% or more is normal for concentrations of general anesthetic drugs that would anesthetize a human. The results indicate that AS-CSF contains a positive allosteric modulator of $GABA_A$ Receptor that would have potent sedative effects in a human. The reversal of this effect by flumazenil suggests that the positive modulator likely acts directly or indirectly at the benzodiazepine binding site on the $GABA_A$ receptor.

Accordingly, patients experiencing disorders associated with excessive sleepiness (e.g., idiopathic or amphetamine resistant hypersomnia) who test positive for a positive allosteric modulator of $GABA_A$ receptor function may likely benefit from administration of flumazenil.

Example 2

Formulation of Flumazenil as Tablet for Sublingual Dosing

| Ingredient: | Amount added: |
| --- | --- |
| Flumazenil | 0.3 grams |
| Tablet triturate base (20%/80% powder) | 4.7 grams |
| Tablet triturate exipient (flavorless) | 2 milliliters |
| Flavor, PCCA Bittershop | 4 drops |
| *Stevia* concentrate (250 mg/mL) | 2 drops |

Procedure: The ingredients were combined and mixed to form a thick paste. After the thick paste was formed, a flavor was added. The flavor added was selected from the following:
a) 2 drops lemon, 1 drop marshmallow, 4 milligrams yellow color
b) 2 drops crème de mint, 4 mg green color
c) 2 drops tangerine, 1 drop marshmallow, 4 mg orange.
The formulation provided 50 tablets.

Example 3

Formulation of Flumazenil as Tablet Triturate for Sublingual Dosing

| Ingredient: | Amount added: |
| --- | --- |
| Flumazenil | 0.6 grams |
| Tablet triturate base (20%/80% powder) | 9.4 grams |
| Tablet triturate exipent (flavorless) | 4 milliliters |
| Flavor, PCCA Bittershop | 8 drops |
| *Stevia* concentrate solution (250 mg/mL) | 4 drops |

Procedure: The ingredients were combined and mixed to form a thick paste. See Example 4 for tablet triturate base (20%/80% powder) formulation and Example 5 for *stevia* concentrate solution formulation. After the thick paste was formed, a flavor was added. The flavor added was selected from the following (quantities given are per 50 tablets):
a) 2 drops lemon, 1 drop marshmallow, 4 milligrams yellow color
b) 2 drops crème de mint, 4 mg green color
c) 2 drops tangerine, 1 drop marshmallow, 4 mg orange
d) 5 drops cherry, 2 drops vanilla, 4 mg red color.
The formulation provided 100 tablets.

Example 4

Formulation of Tablet Triturate Base 20%/80% Powder

| Ingredient: | Amount added: |
| --- | --- |
| Sucrose powdered (confectioners) | 20 grams |
| Lactose monohydrate (hydrous) | 80 grams |

Procedure: The sucrose and lactose monohydrate were sieved through 120 or smaller mesh. After adding the active ingredient (e.g., flumazenil), the mixture was wetted with an excipient of 40% distilled water and 60% alcohol. The formulation provided 100 grams of table triturate base 20%/80% powder.

Example 5

Formulation of *Stevia* Concentrate Solution (250 mg/mL)

| Ingredient: | Amount added: |
| --- | --- |
| *Stevia* powder extract | 25 grams |
| Sodium benzoate | 0.6 grams |
| Water preserved liquid | 100 milliliters |

Procedure: The *stevia* powder and sodium benzoate were dissolved in the water preserved. See Example 6 for water preserved liquid formulation. The mixture was warmed to aid in dissolution. The formulation prepared 100 mL of *stevia* concentrate solution.

Example 6

Formulation of Water Preserved (Paraben) Liquid

| Ingredient: | Amount added: |
| --- | --- |
| Water preserved concentrate liquid | 10 milliliters |
| Water distilled liquid | 3780 mL |

Procedure: The liquids were mixed to prepare the water preserved (paraben) liquid. See Example 7 for water preserved concentrate liquid formulation.

Example 7

Formulation of Water Preserved Concentrate Liquid

| Ingredient: | Amount added: |
| --- | --- |
| Methylparaben | 19 grams |
| Propylparaben NF | 9.6 grams |
| Propylene glycol USP | 100 mL |

Procedure: The ingredients were mixed together and stirred until the methylparaben and propylparaben NF were completely dissolved.

Example 8

Formulation of Flumazenil as Cream for Transdermal Dosing

| Ingredient: | Amount added: |
| --- | --- |
| Flumazenil | 0.04 grams |
| Prophlene glycol USP | 0.1 milligrams |
| Food color, pink (powder) | 0.03 milligrams |
| Versabase cream | 10 grams |

Procedure: The ingredients were combined and mixed. The formulation provided 10 milliliters of cream.

Example 9

Formulation of Flumazenil as Cream for Transdermal Dosing

| Ingredient: | Amount added: |
| --- | --- |
| Flumazenil | 0.25 grams |
| Prophlene glycol USP | 0.25 milliliters |
| Food color, red (powder) | 0.0075 milligrams |
| Versabase cream | 25 grams |

Procedure: The ingredients were combined and mixed. The formulation provided 25 milliliters of cream.

Example 10

Characterization of the Spectrum of $GABA_A$ Receptor Mediated Hypersomnia

An organized, multidimensional approach to characterizing the phenotypic spectrum of GRH will be employed to determine who is affected, and how it manifests with specific attention to overlap with ICSD-2 defined sleep and circadian rhythm disorders. This will involve recruiting and extensively characterizing and correlating biological activity at the $GABA_A$ receptor with behavior in 70 individuals suffering from sleepiness or hypersomnia. Ten, age and sex-matched controls deemed 'affected' or 'unaffected' by sleepiness will also be studied. Initial identification, recruitment, and biological sample procurement will take place in the outpatient clinic and diagnostic sleep laboratory which share dedicated space. After satisfying inclusion/exclusion criteria and upon providing consent, additional behavioral, wake/sleep, and rest-activity cycle assessments will be conducted along with quantification endogenous $GABA_A$ receptor bioactivity. Subjects will then be admitted to a clinical setting for 24 hours and their clinical response to single-blind intravenous delivery of saline, 0.5, and 2.0 mg flumazenil will be determined. Other known causes of hypersomnia, such as hypocretin deficient narcolepsy, exogenous BZD use, iatrogenic effects of common medications known to positively or negatively modulate $GABA_AR$ (e.g., steroids, methylxanthines and many antibiotics), and metabolic disorders (e.g., urea cycle disorders) will be excluded. Finally, to offer some further sense of the commonality and phenotypic spectrum associated with plasma potentiation of $GABA_AR$ function, this activity will be quantified in a population-based sample of subjects.
Inclusion/Exclusion Criteria Patients complaining of daytime sleepiness/hypersomnia with an Epworth Sleepiness Scale or >15 and who exhibit either objective sleepiness (MSL<8 minutes), REM-sleep propensity during their diagnostic evaluation, or treatment resistant sleepiness will be recruited. Patients with DSM-IV Axis I disorders such as depression, bipolar disease, serious medical co-morbidities such as stroke, congestive heart failure, active cancer, severe obstructive pulmonary disease, asthma, or uncontrolled type I or II diabetes will be excluded. Any patient with a history of CNS trauma, infection, or neurodegenerative condition will be excluded. Patients with, treated or untreated sleep disordered breathing (AHI>10) will also be excluded. Subjects with chronic health conditions otherwise well-controlled with medication (e.g., hypertension, hypothyroidism, arthritis) will be allowed to participate. Potential controls and subjects will be excluded if they are ingesting psychoactive medications including sedative-hypnotics, anxiolytics, mood-stabilizers presumed to act via GABAergic mechanisms, neuroleptics, and anti-depressants. In addition, given the known ability of steroids, methylxanthines, and many antibiotics to allosterically modulate $GABA_AR$, potential subjects taking gluco- or mineralo-corticoids, theophylline, or certain antibiotics will be excluded (at least while they are ingesting these agents). Three mls each of plasma and urine will be sent to MedTox Laboratories (Burlington, N.C.) to be analyzed for classic BZDs and their metabolites by gas chromatography (GC) and high performance liquid chromatography (HPLC). The specific agents and respective reporting limits (i.e., thresholds for detection) will include: Desalkylflurazepan (flurazepam metabolite) 10 ng/ml; Nordiazepam 50 ng/ml; oxazepam 50 ng/ml, lorazepam 10 ng/ml, diazepam 50 ng/ml, hydroxyflurazepam 10 ng/ml, temazepam 50 ng/ml, chordiazepoxide, 50 ng/ml, midazolam 10 ng/ml, flurazepam 10 ng/ml, alpha-hydroxyalprazolam 50 ng/ml, alprozolam, 13 ng/ml, hydroxytriazolam 10 ng/ml, triazolam 10 ng/ml and estazolam 10 ng/ml. Additional, individual samples will be sent to NMS Labs (Willow Grove, Pa.) for GC quantification of zolpidem (4-5 ng/ml), HPLC quantification for zaleplon (3 ng/ml), and HPLC tandem mass spectrometry (LC-MS/MS) quantification of eszopiclone.

In order to more carefully delineate a provisional diagnosis of GRH and to provide additional potentially important biochemical data relevant to the spectrum of hypersomnolence disorders such as narcolepsy with cataplexy, CSF for hypocretin (HCRT-1) will be assayed using a commercially available RIA (Orexin A RIA kit, Phoenix Pharmaceuticals, Belmont, Calif.). This assay has an intra-assay variability of <5%. Other recognized metabolic causes of hypersomnolence will also be screened. For example, disorders of the urea cycle and the catabolic enzymes for GABA (e.g., GABA-transaminase and succinic semialdehyde dehydrogenase) have been associated with lassitude and hypersomnia, albeit, incompletely characterized by MSLT or ICSD-2. These must be ruled out as a potential contributors to hypersomnia by assessing arterial ammonia and urine and plasma organic and amino acids. The latter analyses will be performed in a CLIA certified laboratory employing ion exchange chromatography.
Flumazenil Infusion The subject will be instructed in the proper use and care of the Actiwatch and completion of the sleep/wake diary within one month following the lumbar puncture. The subject will complete all study inventories (see below), and within two weeks, will undergo 48-hours of ambulatory polysomnography (see below). Five home/clinic visits will be made during that period to hook-up the subject, check the integrity of the electrodes, and to disconnect the subject from the equipment. Within two weeks, subjects will be scheduled for a 24-hour admission to the ACTSI and after a full-night of recorded sleep receive saline (control), 0.5 mg, and 2.0 mg flumazenil at roughly 2.5 hour intervals while undergoing continuous EEG monitoring and hourly monitoring of vital signs. All subjects will complete a baseline Stanford Sleepiness Scale (SSS) and Psychomotor Vigilance Task (PVT) (see below) which will be repeated at 10, 30, 60, 90, 120, and 150 minutes following each injection.
Polysomnographic Recording Diagnostic nocturnal polysomnography (NPSG) and subsequent daytime testing will b recorded with the Embla digital PSG system (Medcare Corporation, Buffalo, N.Y.) with a sampling rate of 512 Hz, as this allows for Fast Fourier Transform of EEG signals. The system employs a Windows XP platform and uses proprietary software (Somnologica Science). Spectral analyses, or the Welch method of FFT smoothing, that provide an average of several FFT's will be useful to more fully characterize the signature of fingerprint of endogenous $GABA_A R$ like activity given the known effects of GABA on corticothalamic excitability as manifest in the EEG.

Multiple Sleep Latency Testing

Daytime sleepiness will be objectively assessed with the MSLT, which is a clinical and research tool that uses standard guidelines for testing and scoring. Sleep latencies and number of REM onsets will be determined according to standard criteria. The MSLT displays excellent interrater and intrarater reliabilities for sleep latency (coefficients of 0.81-0.88) and REM onset scores (kappa coefficients of 0.78-0.88). The stability of the MSL on repeat testing in known narcoleptics is high (r=0.81, p<0.01) with test-retest reliability improving vis a vis diagnostic certainty with the additional ICSD-2 requirement of two or more sleep onset REM-sleep periods (Kappa=0.95; variance=0.08; Z=2.33; p<0.05).

Blood Collection

Thirty mL of venous blood will be drawn for: 1) lymphoblastoid cell line generation to establish a permanent source of DNA and cells for future investigations; 2) clear plasma aliquoted and frozen for future analytic studies; and 3) buffy coat and purified DNA banked for future genetic studies. The DNA will be purified from 200 μl of buffy coat using a Qiagen kit protocol (Qiagen, Valencia, Calif.). The cell lines, buffy coat, plasma and purified DNA will all be labeled with barcode compatible labels and banked at −80° C. within CRIN dedicated resources. De-identified DNA from all participants will be assigned a 6-digit reference number. Aliquots with this reference number will be forwarded to a laboratory for testing.

Collection of Lumbar CSF

All patients and family members (afflicted, unafflicted) will provide Informed Consent for collection of cerebrospinal fluid (CSF). Lumbar punctures (LP) will be performed under sterile conditions using standard procedures, subcutaneous administration of 4% lidocaine, and collection of 15-20 ml CSF with a 22 gauge spinal needle inserted at L3/L4 or L4/L5. One ml fractions will be labeled with the participants 6-digit reference number and frozen immediately upon dry ice and then stored at −80 degrees Centigrade for future analyses. LPs will be performed between 0830 and 0930 after completion of the first MSLT nap. This will obviate the need to control for subsequent daytime activity levels and extent of food intake which hypothetically could affect endogenous activity at the $GABA_A R$.

Questionnaire Assessments

Administered questionnaires serve as both screening instruments and as predictors in the regression models described below. Subjective sleepiness as a trait variable will be assessed using the Epworth Sleepiness Scale (ESS) and overall quality of sleep will be assessed using the Pittsburgh Sleep Quality Index (PSQI). State and trait anxiety will be assessed with the State-Trait Anxiety Inventory (STAI) and mood will be assessed with the Beck Depression Inventory (BDI). These are all standardized scales with population based norms. Data on functional impairments related to sleepiness using the Functional Outcomes of Sleep Questionnaire (FOSQ) will also be collected. The FOSQ is a self-report measure designed to assess the impact of excessive sleepiness on multiple activities of daily living.

Actigraphy

The Actiwatch wrist-worn monitor, manufactured by Respironics (Murrysville, Pa.), will be used to assess characteristic sleep durations in patients for two weeks prior the infusion protocol. Patients will also be provided a sleep log to keep during the two weeks to generate data on timing of sleep and napping.

Ambulatory Polysomnography

Ambulatory PSG over a 48 hour period will be conducted using the same equipment cited above which can be adapted for this use to document the degree of 'hypersomnia' suggested by actigraphy. Only EEG, EOG, submental EMG lead, ECG, and pulse oxymetry will be conducted. No limb leads will be used for patient safety reasons. Sleep stages, episodes of desaturation, and ECG will be analyzed.

Psychomotor Vigilance Task (PVT)

The Psychomotor Vigilance Task (PVT) provides a sensitive marker of minute-to-minute fluctuations in alertness during the flumazenil infusion protocol. The PVT is a 10-minute, simple, portable reaction time test (finger button press response to light) designed to evaluate the ability to sustain attention and respond in a timely manner to salient signals. Data to be generated include: 1) frequency of lapses, which refer to the number of times the subjects fail to respond to the signal or fail to respond in a timely manner; 2) the median reaction time (RT) over the 10-minute interval. Additionally, as a measure of state sleepiness, the Stanford Sleepiness Scale (SSS) will be administered immediately prior to each trial. The PVT/SSS will be administered at 10, 30, 60, 90, 120, and 150 minutes following each infusion of saline or flumazenil.

Statistical Analysis/Power Calculations

Figure 3:
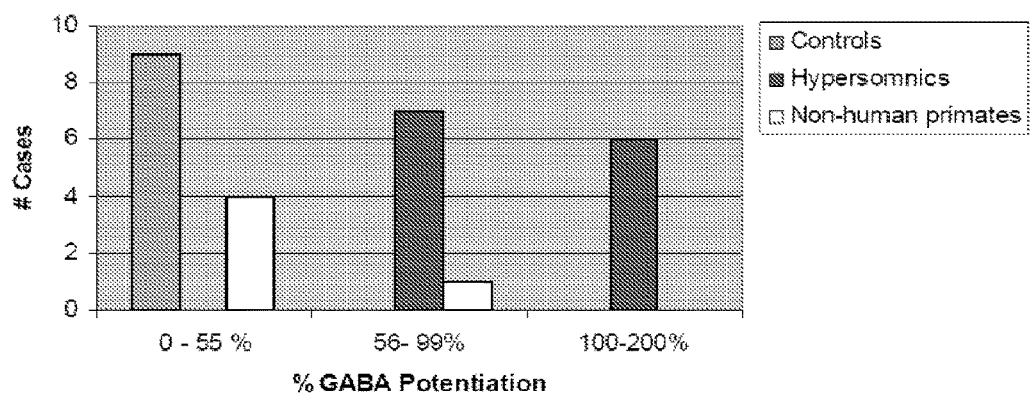
FIG. 3 is a graph illustrating that potentiation of $GABA_A$ function is evident in human controls absent sleep related complaints, non-human (rhesus) primates, and in excess in many hypersomnic patients.

The relationship between the extent of $GABA_A$ potentiation and behavioral outcomes will be examined using regression models. Separate models will be run for each type of specimen source (e.g., CSF and plasma derived markers of potentiation). A simple bivariate relationship between the two measures of GABA potentiation using correlational models will be examined, relying on non-parametric alternatives (Spearman) should the measure present with a non-normal distribution. The extent of GABA potentiation in the Baseline condition among patients will be predicted using predictors such as standard demographics (e.g., gender, age), psychometrics (e.g., STAI, BDI), recent sleep history (e.g., cumulative sleep over the preceding 2 weeks as measured with actigraphy, daytime naps on sleep log), and laboratory-based measurements of nocturnal sleep (e.g., FFT derived relative delta power or beta power) or daytime alertness (e.g., MSLT sleep latency, PVT-derived median reaction time). Because multiple measurements in each domain and the sheer number of domains increase the likelihood of Type I error, such error will be minimized by first carefully examining the intercorrelations among measures within each domain. Substantial collinearity is expected to be among many of these. For example, trait anxiety (STAI) and depressed mood (BDI) are likely to be highly intercorrelated, as are Baseline PVT median reaction times and MSLT-defined sleep latency. The specific approach to deriving variables to employ in the regression might include a selection of a single variable from each domain chosen on the basis of a more normally distributed range of scores across subjects. Alternatively, the data reduction techniques can be relied on such as principal components analyses (PCA) to determine a single measure in each domain that best captures variance within that domain. Thus, a single score (or composite score, if PCA was used) from each domain will be entered in the regression predicting potentiation. Based on the data presented in FIG. 3, large effects will be displayed. GABA potentiation differences between controls and patients will be substantial (d=3.095). Assuming effects of this size are maintained in the work proposed here, and assuming a 2-tailed alpha of 0.01, an N of 60 cases would yield 99% power to reject the null of hypothesis of the contribution for any single domain to GABA potentiation. It is fully recognized that, in multivariate models encompassing each of the five domains listed above, actual power might be somewhat reduced because of the contribution of multiple variables to the prediction. Nonetheless, given the substantial effects observed in FIG. 3, sufficient power to understand how different variables may predict potentiation when considered simultaneously should be retained. Regression models will also be used to determine what factors may predict change in GABA potentiation under flumazenil infusion. Each patient's Baseline potentiation level (measured under saline infusion) will be forced and it is determined whether either low or high dosage of flumazenil predicts change subsequent to infusion. Domain variables selected for entry into these models are limited only to those shown to relevant to the prediction of Baseline potentiation, thus saving degrees of freedom whenever possible. This modeling allows the determining of the extent that other variables (demographic, recent sleep history, etc) may have to moderate or mediate the GABA-mediated response to flumazenil. The behavioral response to flumazenil (performed separately by dose) will also be examined, defined as the mean of the median RTs for the 4 PVT measurements closest to point of infusion. Each patient's Baseline median RT (mean of 4 Baseline/saline measurements) (see FIGS. 6, 8, 10, and 12) and Baseline GABA potentiation levels will be forced initially in these regressions, followed by entry of significant predictors of Baseline potentiation found in the analyses described above.

Further, the plasma-measured GABA potentiation will be examined as the dependent variable among 227 individuals, all of whom will have received two nights of PSG and an intervening day of MSLT. The hypersomnolence demonstrated by the index cases will represent a more extreme form of a continuous trait present in segment of the population generally. To that end, the initial review of the data indicated that 58 had mean MSLT-defined sleep latencies of less than 5 minutes that could not be accounted for by known sleep disorders. If the MSLTs across all 227 cases show a bimodal distribution, the analyses would be limited to only those cases at the extremes (e.g., mean latencies <5 minutes versus mean latencies >15 minutes) and employing an ANCOVA approach. However, the distribution of mean sleep latencies is more continuous and, as is often the case of studies using MSLT, sharply skewed to the right. In this case, log transforms are performed on these mean values before proceeding. The overall approach will be similar to those described above, though they are somewhat more limited by the range of variables collected.

Example 11

Electroencephalography (EEG) Power Spectrum Analysis

Quantitative analysis of delta (0.4-3.99 Hz), theta (4.00-7.99 Hz), alpha (8.00-12.99 Hz) and beta power (13.00-16.00 Hz) was obtained from EEG spectral analyses of the C4-M1 electrode. Manual and automated artifact removal methods were utilized prior to EEG spectral analyses to prevent erroneous results. Spectral analyses were conducted utilizing the computational software program MATLAB v 7.1. The Welch method of FFT smoothing was employed to obtain power spectrum values from an average of several FFT's. The FFT contained a minimum of 512 data samples with a 50% overlap moving window of the subsequent 512 data samples. EEG data collected at 200 Hz provided an FFT window comprised of approximately 2.56 seconds of data. Parameters for Welch spectral analyses were user adjustable within the MATLAB program such that user defined frequency bands for specific frequency resolutions were obtained. Power values for the defined frequency bands were represented by $mV^2/Hz$ (microvolts squared divided by hertz).

Figure 4:
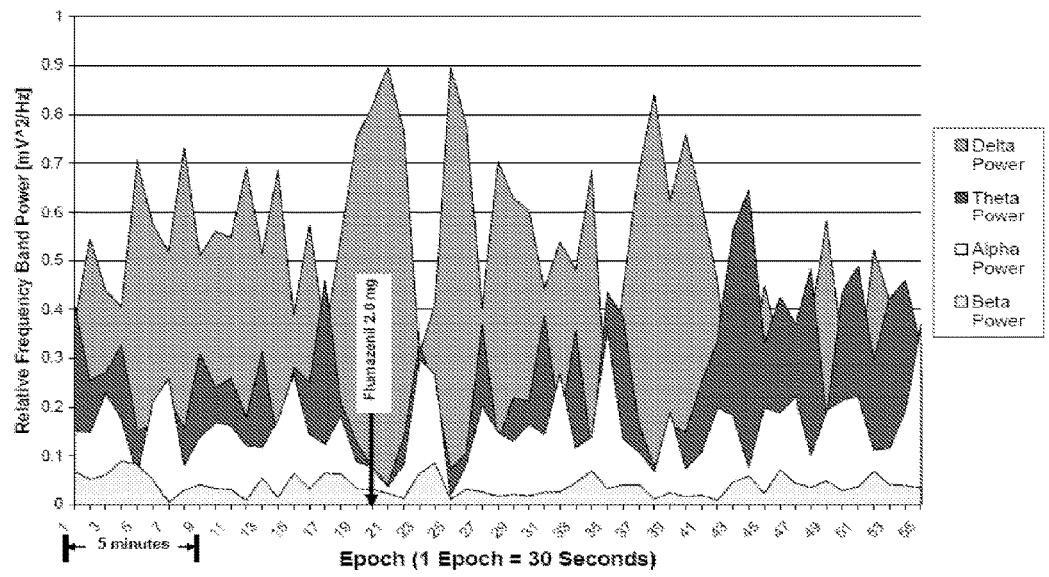
FIG. 4 shows the power spectrum analyses results obtained from processing 27 minutes of non-artifactual data for subject DS122 after infusion with 2.0 mg flumazenil.
Figure 5:
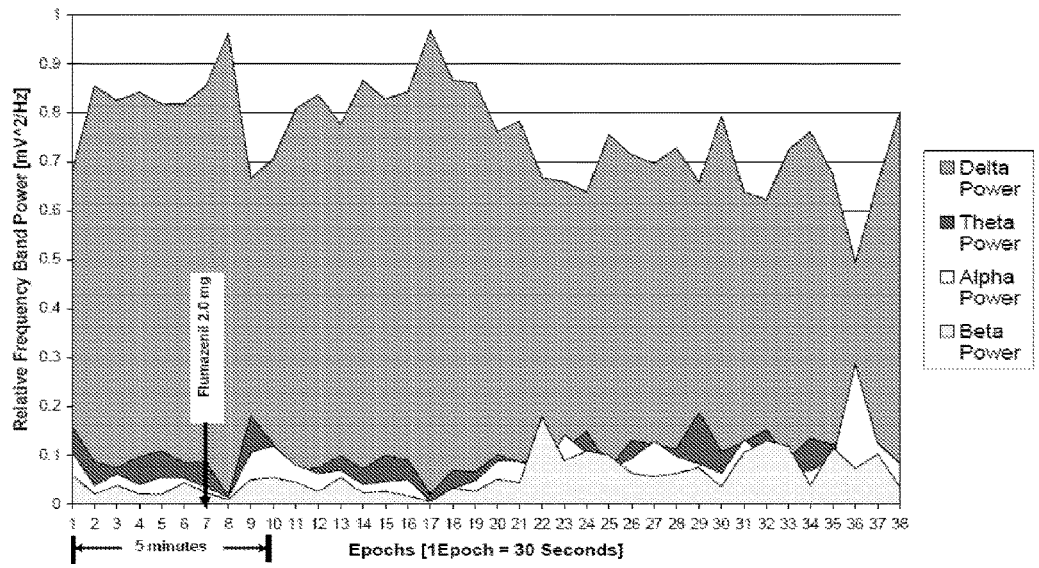
FIG. 5 shows the power spectrum analyses results obtained from processing 19 minutes of non-artifactual data for subject DT74 after infusion with 2.0 mg flumazenil.
Figure 6:
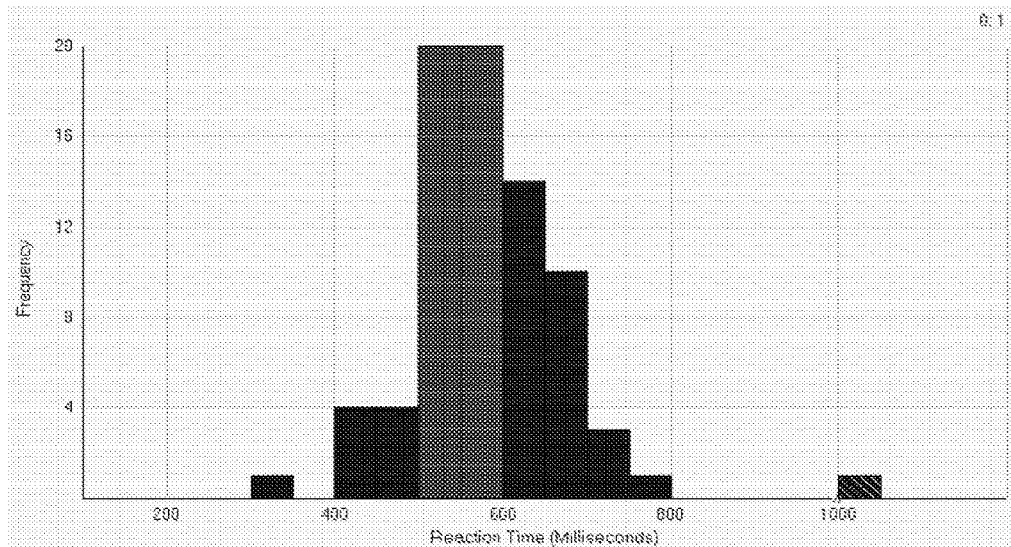
FIG. 6 shows a histogram displaying the results of the psychomotor vigilance task (PVT) performance before administration of I.V. flumazenil for case 74.
Figure 7:
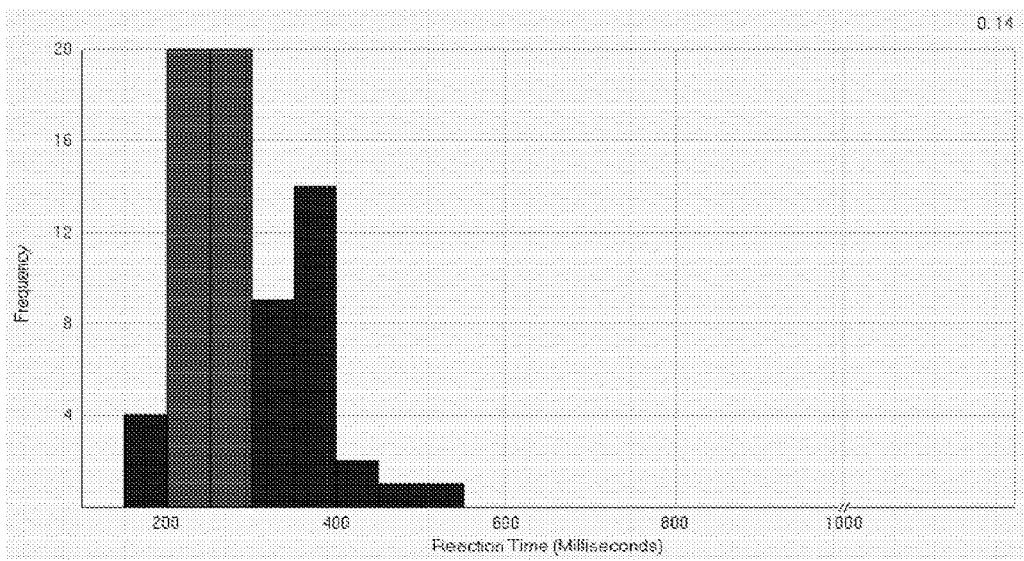
FIG. 7 shows a histogram displaying the results of the psychomotor vigilance task (PVT) performance after 2.0 mg dose of I.V. flumazenil for case 74.
Figure 8:
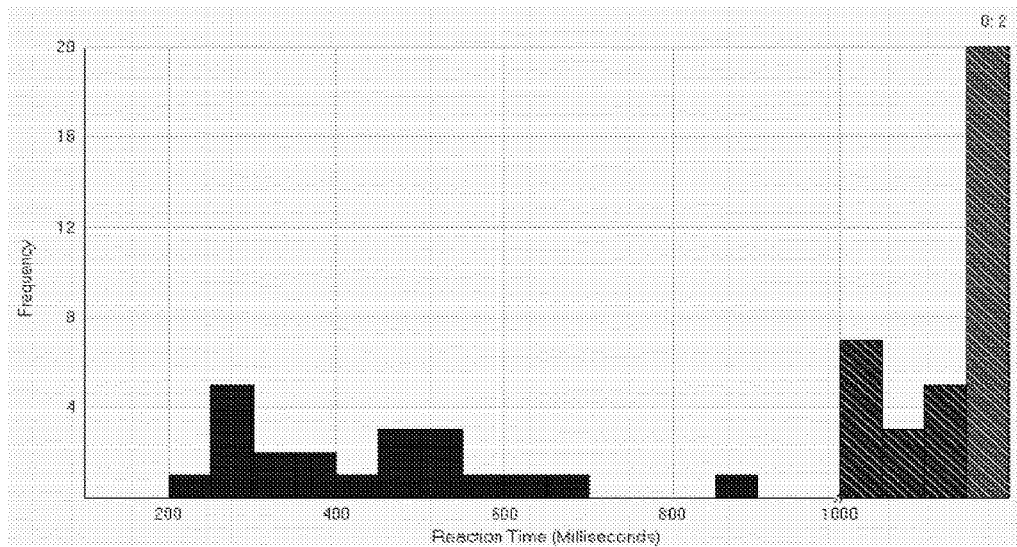
FIG. 8 shows a histogram displaying the results of the psychomotor vigilance task (PVT) performance before administration of I.V. flumazenil for case 102.
Figure 9:
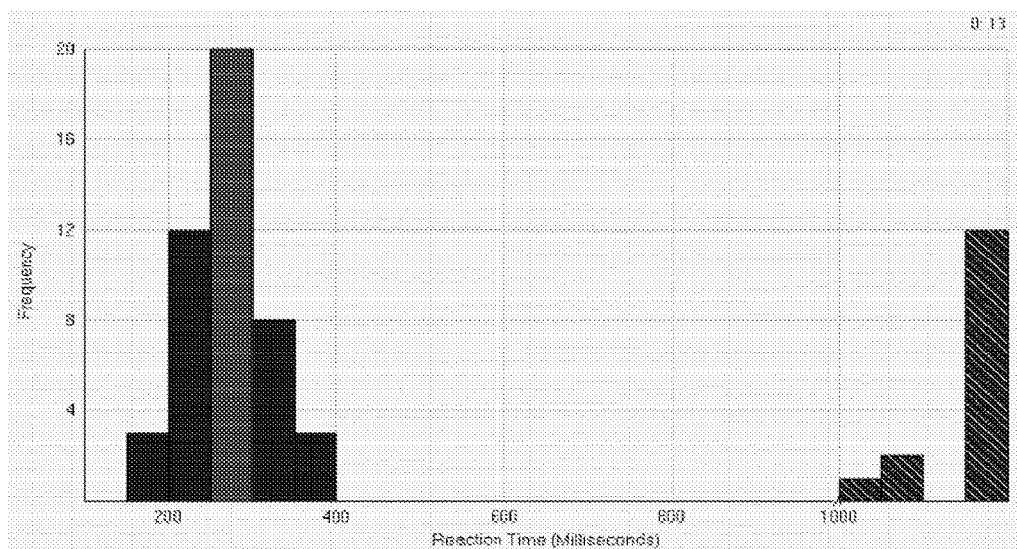
FIG. 9 shows a histogram displaying the results of the psychomotor vigilance task (PVT) performance after 2.0 mg dose of I.V. flumazenil for case 102.
Figure 10:
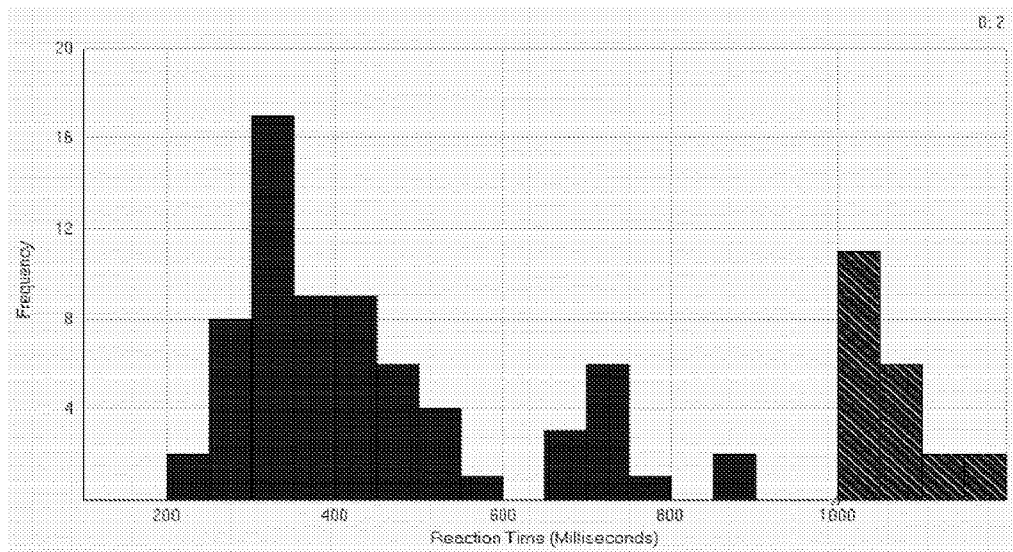
FIG. 10 shows a histogram displaying the results of the psychomotor vigilance task (PVT) performance before administration of I.V. flumazenil for case 122.
Figure 11:
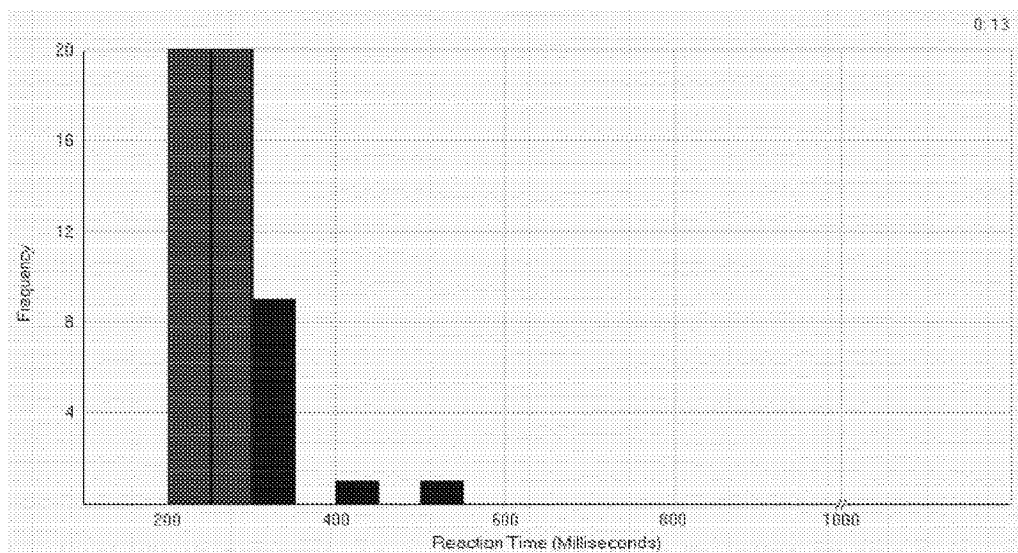
FIG. 11 shows a histogram displaying the results of the psychomotor vigilance task (PVT) performance after 2.0 mg dose of I.V. flumazenil for case 122.
Figure 12:
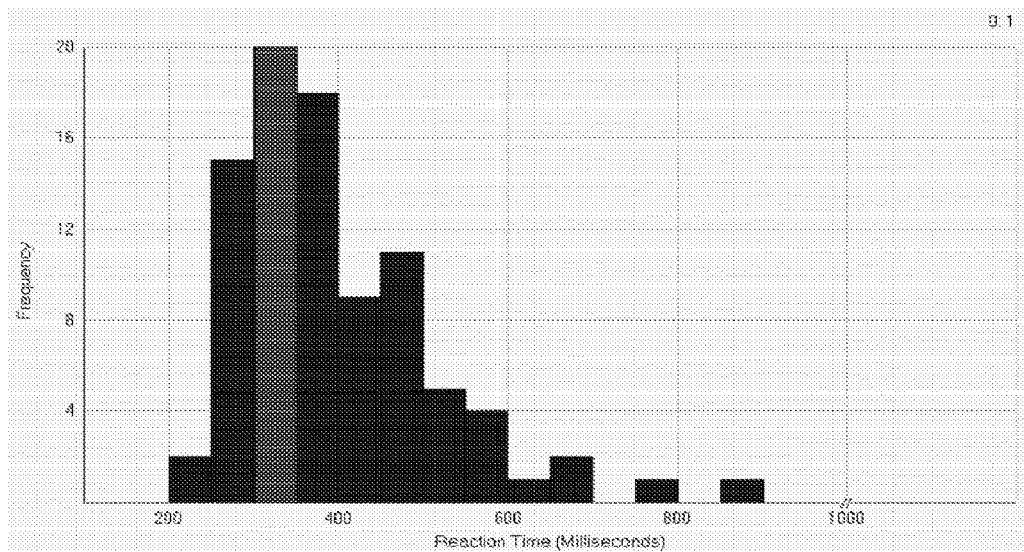
FIG. 12 shows a histogram displaying the results of the psychomotor vigilance task (PVT) performance before administration of I.V. flumazenil for case 124.
Figure 13:
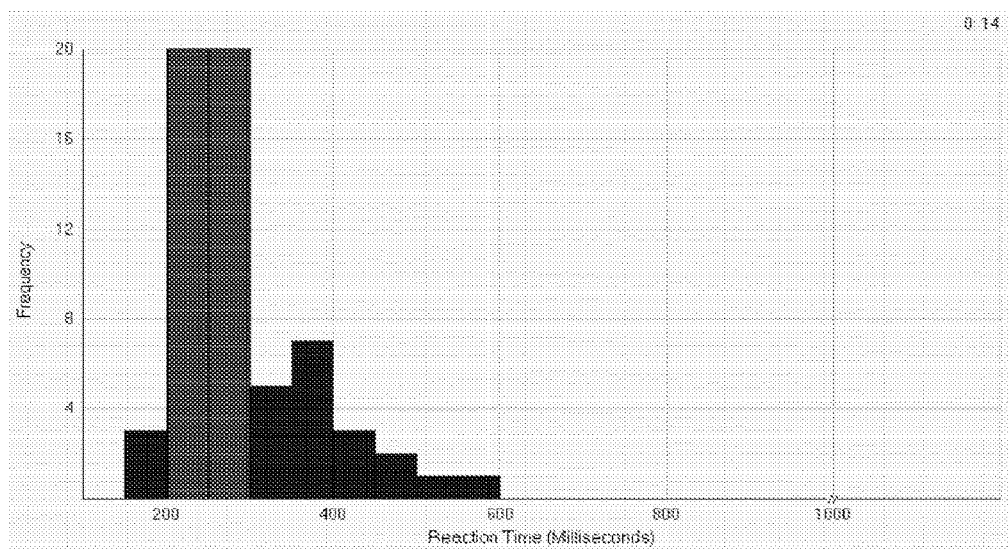
FIG. 13 shows a histogram displaying the results of the psychomotor vigilance task (PVT) performance after 1.2 mg dose of I.V. flumazenil for case 124.
Figure 14:
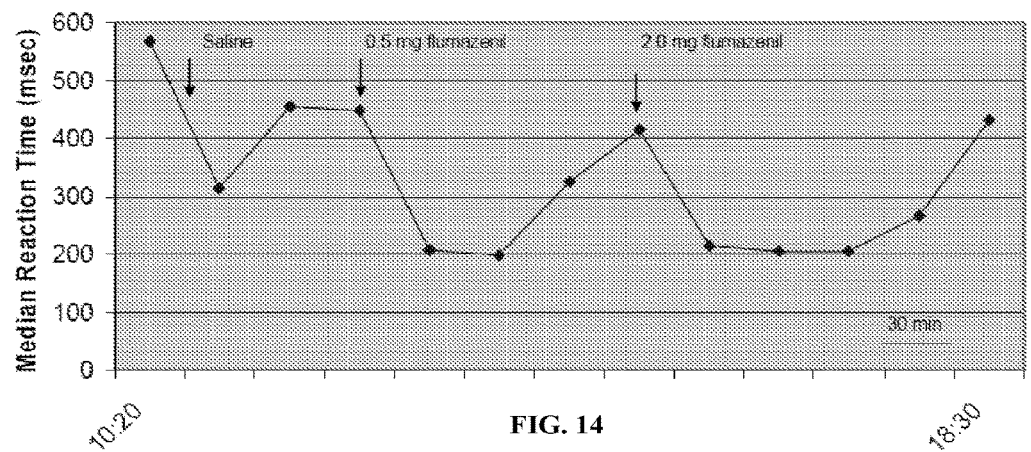
FIG. 14 shows a graph displaying the results of the psychomotor vigilance task (PVT) performance before and after treatment with I.V. flumazenil for case 74.
Figure 15:
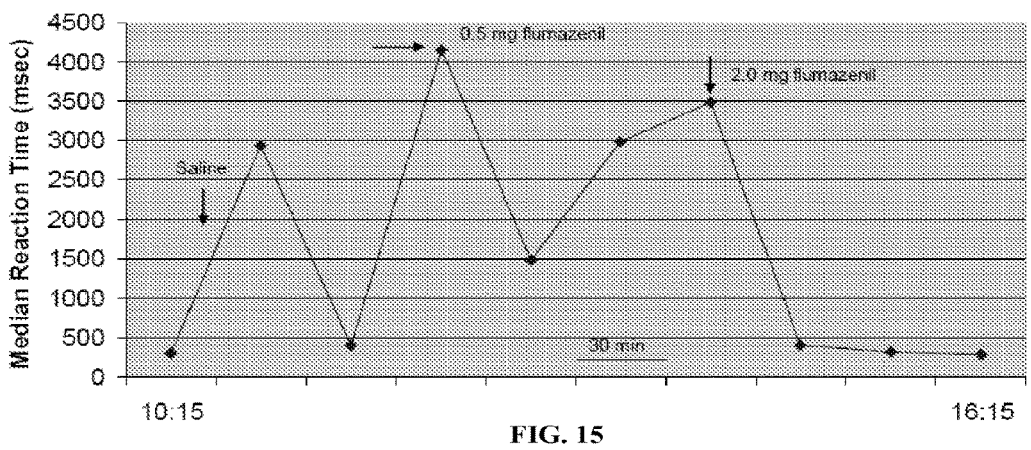
FIG. 15 shows a graph displaying the results of the psychomotor vigilance task (PVT) performance before and after treatment with I.V. flumazenil for case 102.
Figure 16:
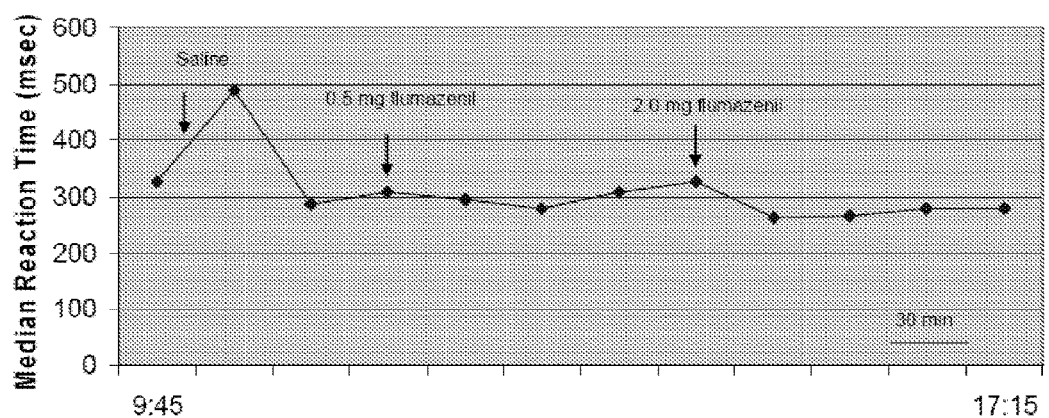
FIG. 16 shows a graph displaying the results of the psychomotor vigilance task (PVT) performance before and after treatment with I.V. flumazenil for case 122.
Figure 17:
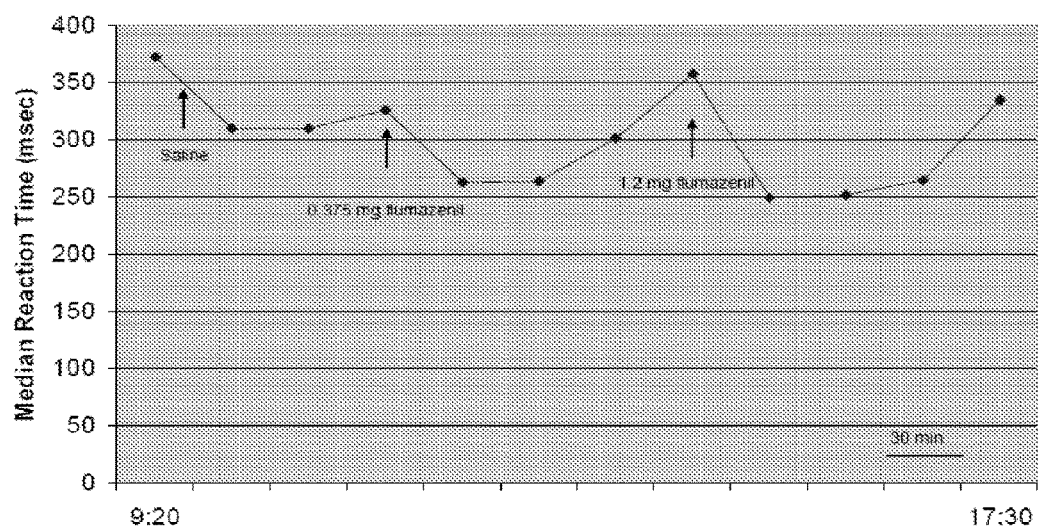
FIG. 17 shows a graph displaying the results of the psychomotor vigilance task (PVT) performance before and after treatment with I.V. flumazenil for case 124.

The EEG power spectrum analyses for two subjects (DS122 and DT74) were obtained (see FIGS. 4 and 5, respectively). Table 1 provides the corresponding sampling frequency and FFT window size for each patient data set. There was a spectral change approximately five minutes after intravenous infusion of 2.0 mg flumazenil that manifested as diminution of delta frequencies and emergence of higher EEG frequencies emblematic of improved vigilance/arousal.

TABLE 1

| Patient | Sampling Frequency | FFT size |
| --- | --- | --- |
| DS | 500 Hz | 1024 |
| DT | 200 Hz | 512 |

Table 2 displays mean relative band power results obtained from EEG power spectrum (i.e., delta, theta, alpha, beta) analyses of subject ED102 and DS122 for each clinical treatment (i.e., saline, 0.5 mg flumazenil, and 2.0 mg flumazenil). Ten minute data segments were selected 30 minutes following each clinical treatment and were analyzed via a three second processing window to obtain the relative power spectrum results provided in Table 2.

TABLE 2

| Subject | Treatment | Delta Power | Theta Power | Alpha Power | Beta Power | Gamma Power |
| --- | --- | --- | --- | --- | --- | --- |
| ED102 | Saline | 0.5314 | 0.1824 | 0.1090 | 0.1207 | 0.0565 |
| ED102 | 0.5 mg flumazenil | 0.5199 | 0.1755 | 0.1017 | 0.1387 | 0.0642 |
| ED102 | 2.0 mg flumazenil | 0.4820 | 0.1479 | 0.0866 | 0.1803 | 0.1032 |
| DS122 | Saline | 0.4122 | 0.2777 | 0.1966 | 0.1011 | 0.0124 |
| DS122 | 0.5 mg flumazenil | 0.3515 | 0.2995 | 0.2183 | 0.1165 | 0.0142 |
| DS122 | 2.0 mg flumazenil | 0.3128 | 0.3776 | 0.1798 | 0.1141 | 0.0157 |

Example 12

Psychomotor Vigilance Task (PVT)

The dose and temporal reversibility of the sleepiness of patients to intravenous flumazenil were determined employing the PVT/SSS paradigm as described in Example 10. Five hypersomnic patients demonstrated dose-dependent improvements in vigilance and subjective alertness with intravenous delivery of flumazenil as shown in Table 3.

TABLE 3

| | | | | Stanford | | | | | | |
| | % | Reaction | | Sleepiness | FLU 0.325-0.5 mg | | | FLU 1.2-2 mg | | |
| Case | GABA potentiation | time (RT) in ms | lapses | Scale (SSS) | RTs in ms | lapses | SSS | RTs in ms | lapses | SSS |
| --- | --- | --- | --- | --- | --- | --- | --- | --- | --- | --- |
| 74 | 200 +/− 21.7 | 432.3 +/− 84.8 | 31.0 | 6 | 236.8 +/− 47.7 | 0.7 | 4 | 207 +/− 4.97 | 0.7 | 3 |
| 99 | 160 +/− 9.2 | 285.5 +/− 13 | N/A | 6 | 255.8 +/− 6.3 | N/A | 3 | 225.5 +/− 2.3 | N/A | 1 |
| 102 | 189 +/− 24.3 | 1962 +/− 1478 | 16.4 | 6 | 1642 +/− 1036 | 3.1 | 3 | 363.2 +/− 38.2 | 3.8 | 4 |
| 122 | 149 +/− 20.4 | 369.5 +/− 78.9 | 17.2 | 5 | 297.8 +/− 16.2 | 0.6 | 1 | 269.3 +/− 6.8 | 0.6 | 1 |
| 124 | 58.5 +/− 3.5 | 327.8 +/− 22.96 | 5.8 | 6 | 259.8 +/− 3.8 | 1.3 | 2 | 250 +/− 1.2 | 1.0 | 2 |

Administration of flumazenil (FLU) was associated with dramatic and substantial improvement in reaction time performance on the PVT and subjective alertness on the SSS. Relative to baseline, median RTs decreases at low ($t=2.56$, $p=0.063$) dose, and number of lapses decreased both at low ($t=3.03$, $p=0.056$) and high ($t=3.51$, $p=0.039$) dose. When compared to the worst Baseline measure for each case, SSS showed significant improvement for both low ($t=8.55$, $p=0.001$) and high ($t=7.06$, $p=0.002$) dose. Raw histograms for cases 74, 102, 122, and 124 displaying baseline PVT performance and PVT performance after 2.0 mg are shown in FIGS. 6-17.

Example 13

Clinical Study of $GABA_A$ Receptor Mediated Hypersomnia (GRH)

Figure 18A:
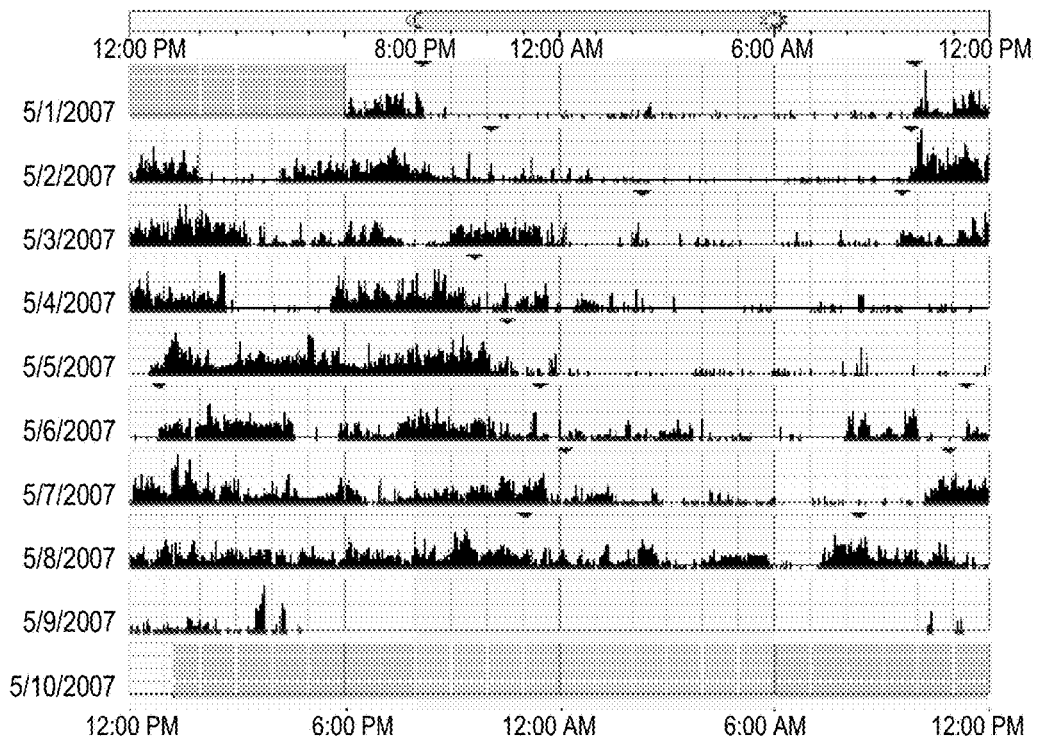
FIG. 18a is an illustration of the rest-activity cycle of patient AS99 before treatment with flumazenil.
Figure 18B:
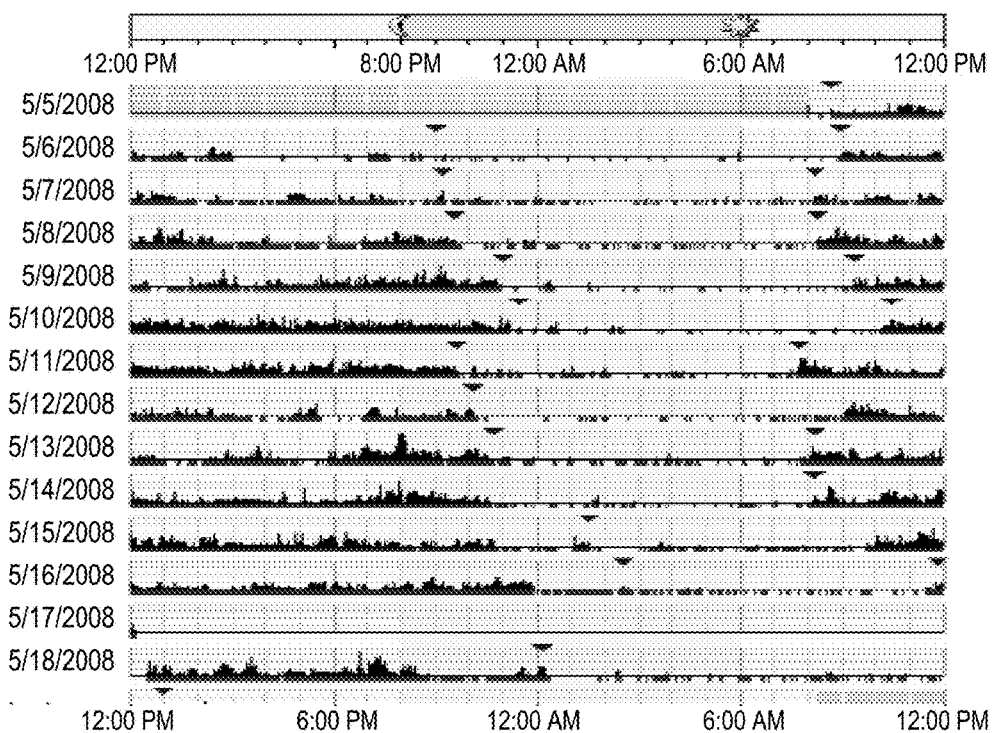
FIG. 18b is an illustration of the rest-activity cycle of patient AS99 after treatment with flumazenil.

Patient AS99 with a diagnosis of "narcolepsy" and restless legs syndrome (RLS) complained of "craving" sleep, and of long, unrefreshing sleep periods. Polysomnography revealed periodic leg movements (31 per hour), but was otherwise normal (TST=444 min). A mean sleep nap latency of 2.6 minutes absent intrusion of REM sleep confirmed pathological sleepiness and a diagnosis of idiopathic hypersomnia. Patient AS99's examination was normal with a BMI of 22.3, and urine drug screens (repeated×3), serum ammonia (n=2), thyroid functions (n=2), complete blood counts (n=5), vitamin B12, and comprehensive metabolic screens (n=2) were normal. Ferritin (23 ng/ml) and % transferrin saturation (13%) were low with otherwise normal serum iron. The RLS was successfully treated with iron supplementation and pramipexole; however, hypersomnia persisted despite maximum doses of dextroamphetamine (60 mg) in combination with modafinil (800 mg). Actigraphy confirmed resolution of RLS/PLMs, yet revealed erratic rest-activity cycles with sleep periods varying from 5 to 10 hours per night. Patient AS99's condition progressed and weight decreased (BMI=20), and patient AS99 developed anxiety and hypertension requiring treatment with metoprolol attributed to supratherapeutic doses of psychostimulants. Affective and factitious disorders were ruled out by two independent psychiatric assessments. Weaned off all medications, CSF was obtained and hypocretin determined to be high-normal (401 pg/ml) thus ruling out a diagnosis of narcolepsy. Electrophysiological analysis for bioactivity in CSF and plasma revealed the presence of a positive allosteric modulator of the $GABA_A$ receptor reversible with the competitive BZD antagonist flumazenil. The dose and temporal reversibility of sleepiness to intravenous flumazenil were then determined employing the PVT/SSS paradigm. The rest-activity cycles of patient AS99 improved with chronic sublingual flumazenil administration (see FIGS. 18a and 18b). The sleep, mood, sleepiness, and quality of life improved dramatically and are sustainable with sublingual flumazenil in patient AS99 (see Table 4) as shown through the Pittsburgh Sleep Quality Index, Beck Depression Inventory, Epworth Sleepiness Scale, Functional Outcomes of Sleep, and SF-36 Health Survey.

TABLE 4

| Variable | February 22nd (pre-treatment) | March 31st (1 month post) | April 28th (2 months post) |
| --- | --- | --- | --- |
| Pittsburgh Sleep Quality Index | 4 | 2 | 1 |
| Beck Depression Inventory | 7 | 2 | 2 |
| Epworth Sleepiness Scale | 18 | 3 | 3 |
| Functional Outcomes of Sleep | | | |
| General Productivity | 6 | 23 | 24 |
| Social Activity | 12 | 24 | 24 |
| Activity | 3.6 | 19.6 | 21.3 |
| Vigilance | 8 | 22 | 24 |
| Total | 29.5 | 88.6 | 93.3 |
| Total Mean | 7.4 | 22.1 | 23.3 |
| SF-36 Health Survey | | | |
| Physical | 39.5 | 54.4 | 66.2 |
| Mental | 49.7 | 64.0 | 56.2 |

Patient AS99 continued use of sublingual flumazenil for 9 months with positive results. When prescribed clarithromycin, patient AS99 suddenly developed 4 nights of insomnia that reversed promptly upon discontinuation. Clarithromycin is an antibiotic with a high incidence of hypomania/insomnia associated with its use, and it functions as a negative allosteric modulator at $GABA_A$ receptors.

Example 14

Identification of Substance Causing Potentiation at $GABA_A$ Receptors

Several studies were performed in order to identify the substance accounting for potentiation at $GABA_A$ receptors. It was determined that adenosine is not the substance, as several concentrations (1 mM, 100 μM, and 10 μM) of adenosine in artificial CSF exhibited no activity at $GABA_A$ receptors.

In addition, it was shown that the substance accounting for potentiation at $GABA_A$ receptors is not a neurosteroid. Cerebrospinal fluid from four hypersomnic cases were tested in duplicate by quantitative HPLC for endogenous neuroactive GABAergic steroids (i.e., neurosteroids). The controls revealed no differences in the levels of pregnenolone, DHEA, 3α,5α-THP, 3α,5β-androstandiol, 3α,5α-androsterone, and 3α,51β-androsterone. Controls and subjects exhibited undetectable quantities of 3α,5β-THP, 3α,5α-THDOC, 3α,5β-THDOC, and 3α,5α-androstandiol.

Further, it was shown that the substance accounting for potentiation at GABA$_A$ receptors has a molecular weight less than 3,000. Pooled CSFs from confirmed GRH subjects versus controls were fractionated with filters having approximately 3,000 molecular weight cut-off. Bioactivity at GABA$_A$ receptors in both samples was completely retained within the smaller molecular weight fractions.

It was also found that the substance accounting for potentiation at GABA$_A$ receptors may act at a non-traditional benzodiazepine site (see FIGS. 19a and 19b). In a whole cell patch clamp current recording from a cell expressing human α1β2γ2s receptors, the response to 10 μM GABA is potentiated by the co-application of a 50% CSF, indicating the presence of a positive allosteric modulator (see FIG. 19a). A recording from a different cell expressing the benzodiazepine insensitive subunit α1(H102R) shows that the enhancement persists (see FIG. 19b). Not to be bound by theory, this data indicates that the somnogenic compound is not a classical benzodiazepine, or does not act conventionally at the classical high-affinity benzodiazepine binding site on the GABA$_A$ receptor.

Example 15

Patch Clamp Analysis of CSF Bioactivity

Patch clamp analyses of CSFs from non-human primates, drawn from animals under different conditions, was also used to identify the somnogenic GABAergic substance. In this experiment, CSF was drawn from 4 monkeys (Canjala, Santiaga, Penelope, and Cricket) at 3 different time points. 1) early morning, 2) late afternoon and 3) very late evening, having been kept awake throughout (when they would normally be asleep). A whole cell patch clamp current was recorded (as described in Example 1), and the response to 10 μM GABA co-administered with primate CSF was determined. The bioactivity of the CSF is expressed as a percent increase, or potentiation, of the control current by the CSF (see Table 5). The first two columns show the normal diurnal variation of this somnogenic compound. It appears that this substance waxes and wanes in animals as it does in humans during the normal day night cycle. More interestingly, in 2 of the 4 animals, the bioactivity increased still further after the animals were "wake-extended". These promising results indicate that under sleep deprived conditions, humans may also benefit from flumzenil or other GABAergic therapy to relieve the symptoms of fatigue they experience from the accumulation of this somnogenic compound.

TABLE 5

|  | Morning | Evening | Wake Enhanced |
| --- | --- | --- | --- |
| Canjala | 79.9 ± 2.7 | 76.6 ± 4.6 | 73.4 ± 4.7 |
| Santiaga | 49.0 ± 2.0 | 58.7 ± 0.8 | 64.9 ± 1.7 |
| Penelope | 54.6 ± 3.5 | 77.1 ± 0.5 | 98.4 ± 23.1 |
| Cricket | 51.3 ± 0.7 | 58.1 ± 4.2 | 63.9 ± 6.9 |

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating hypersomnia, the method comprising administering an effective amount of a GABA$_A$ receptor antagonist to a subject having hypersomnia, wherein the GABA$_A$ receptor antagonist is administered transmucosally or transdermally, and wherein the GABA$_A$ receptor antagonist is selected from the group consisting of flumazenil, clarithromycin, picrotoxin, bicuculline, cicutoxin, and oenanthotoxin.

2. The method of claim 1, wherein the GABA$_A$ receptor antagonist is flumazenil or clarithromycin.

3. The method of claim 1, wherein the transmucosal administration of the GABA$_A$ receptor antagonist is combined with the transdermal administration of the GABA$_A$ receptor antagonist.

4. The method of claim 1, wherein the GABA$_A$ receptor antagonist is administered transmucosally in a tablet, packaged powder, edible film strip, soft gel capsule, hard gel capsule, lozenge, or troche.

5. The method of claim 1, wherein the GABA$_A$ receptor antagonist is administered transmucosally in a unit dosage form comprising from about 0.5 mg to about 20 mg of the GABA$_A$ receptor antagonist.

6. The method of claim 5, wherein the GABA$_A$ receptor antagonist is administered transmucosally in a unit dosage form comprising about 6 mg of the GABA$_A$ receptor antagonist.

7. The method of claim 1, wherein the GABA$_A$ receptor antagonist is administered transmucosally at a daily dosage from about 1 mg per BMI to about 5 mg per BMI.

8. The method of claim 1, wherein the GABA$_A$ receptor antagonist is administered transdermally in an ointment, an emulsion, a lotion, a solution, a cream, a gel, or a patch.

9. The method of claim 1, wherein the GABA$_A$ receptor antagonist is administered as a daily dose.

10. The method of claim 9, wherein the GABA$_A$ receptor antagonist daily dose is divided equally into two to six times per day daily dosing.

11. The method of claim 1, wherein the subject was not administered a benzodiazepine.

12. The method of claim 1, wherein the subject was not administered midazolam.

13. The method of claim 1, wherein the subject has a measured Epworth sleepiness scale of greater than 15.

14. A method of treating hypersomnia in a human subject, the method comprising administering an effective amount of a GABA$_A$ receptor antagonist to the human subject, wherein the GABA$_A$ receptor antagonist is administered transdermally, transmucosally, sublingually, or subdermally, wherein the GABA$_A$ receptor antagonist is selected from the group consisting of flumazenil, clarithromycin, picrotoxin, bicuculline, cicutoxin, and oenanthotoxin.

15. The method of claim 14, wherein the GABA$_A$ receptor antagonist is flumazenil or clarithromycin.

16. The method of claim 14, wherein the subject had hypersomnia over the course of a year or more prior to being administered with the GABA$_A$ receptor antagonist.

17. The method of claim 14, wherein a cerebrospinal fluid (CSF) or blood sample from the subject having hypersomnia potentiates the response of GABA on GABA-induced currents in a cell expressing a GABA$_A$ receptor.

18. The method of claim 14, wherein the GABA-induced currents in the cell expressing the GABA$_A$ receptor are measured by a whole cell patch clamp.

19. The method of claim 14, wherein the expressed GABA$_A$ receptor is a recombinant human GABA$_A$ receptor.

* * * * *